(12) United States Patent
Ozaki et al.

(10) Patent No.: US 11,039,740 B2
(45) Date of Patent: Jun. 22, 2021

(54) OPHTHALMIC APPARATUS

(71) Applicant: NIDEK CO., LTD., Gamagori (JP)

(72) Inventors: Yoshihiro Ozaki, Nukata-gun (JP); Toru Arikawa, Nukata-gun (JP); Hiroyuki Umano, Toyohashi (JP)

(73) Assignee: NIDEK CO., LTD., Gamagori (JP)

( * ) Notice: Subject to any disclaimer, the term of this patent is extended or adjusted under 35 U.S.C. 154(b) by 1 day.

(21) Appl. No.: 15/610,919

(22) Filed: Jun. 1, 2017

(65) Prior Publication Data

US 2017/0347872 A1  Dec. 7, 2017

(30) Foreign Application Priority Data

Jun. 3, 2016 (JP) .............................. JP2016-112274
Jun. 3, 2016 (JP) .............................. JP2016-112275
Jun. 3, 2016 (JP) .............................. JP2016-112276

(51) Int. Cl.
*A61B 3/00* (2006.01)
*A61B 3/10* (2006.01)
(Continued)

(52) U.S. Cl.
CPC .......... *A61B 3/0083* (2013.01); *A61B 3/0025* (2013.01); *A61B 3/10* (2013.01);
(Continued)

(58) Field of Classification Search
CPC ........... A61B 2017/00199; A61B 2017/00694; A61B 2017/00973; A61B 3/13; A61B 3/0025; A61B 3/0033; A61B 3/0058; A61B 3/14; A61B 3/18; A61B 3/0083; A61B 3/10; A61B 3/152; A61B 5/0077; A61B 5/1103; A61B 6/14; A61B 6/032; A61B 6/04; A61B 6/0421; A61B 3/0075; A61B 3/103; A61B 3/165; A61B 6/08;
(Continued)

(56) References Cited

U.S. PATENT DOCUMENTS 5,387,952 A * 2/1995 Byer .................... A61B 3/0083
340/573.7
5,909,269 A 6/1999 Isogai et al.
(Continued)

FOREIGN PATENT DOCUMENTS

CN 101507601 A 8/2009
EP 1442698 A1 8/2004
(Continued)

OTHER PUBLICATIONS

Feb. 1, 2018 Extended European Search Report issued in Patent Application No. 17173945.1.
(Continued)

*Primary Examiner* — Brandi N Thomas
(74) *Attorney, Agent, or Firm* — Oliff PLC

(57) ABSTRACT

An ophthalmic apparatus for examining an examinee's eye, comprising a face support member to support an examinee's face, a human detection member to detect whether or not the face is supported by the face support member, a notification member to give an announcement to an examinee or an examiner, and a control member to control the notification member based on a detection result of the human detection member.

12 Claims, 15 Drawing Sheets

(51) Int. Cl.
*A61B 3/15* (2006.01)
*G06K 9/00* (2006.01)
*A61B 5/00* (2006.01)
*A61B 5/11* (2006.01)

(52) U.S. Cl.
CPC .......... *A61B 3/152* (2013.01); *G06K 9/00604* (2013.01); *A61B 5/0077* (2013.01); *A61B 5/1103* (2013.01)

(58) Field of Classification Search
CPC ......... A61B 6/4441; A61B 3/00; A61B 3/024; A61B 3/08; A61B 3/085; G06F 3/012; G06F 3/017; G06F 3/167; G06F 3/011; G06F 3/0346; G06F 3/04815; G06F 3/165; G06F 2200/1637; G06F 3/013; G06F 3/0304; G06F 1/163; G06F 1/1686; G06F 3/016; G06F 3/03547; G06F 3/0362; G06F 3/0488; G06F 3/16; G06F 9/542; H04N 21/4223; H04N 21/2187; H04N 21/2385; H04N 21/4122; H04N 21/4318; H04N 21/4363; H04N 21/44008; H04N 21/4402; H04N 21/440263; H04N 21/44218; H04N 21/6106; H04N 21/8146; H04N 5/23229; H04N 5/23232; H04N 7/173; H04N 5/265; H04N 5/64
USPC ........ 351/200, 205–206, 209–211, 221, 222, 351/223, 243–245
See application file for complete search history.

(56) References Cited

U.S. PATENT DOCUMENTS

| | | | |
|---|---|---|---|
| 6,309,068 | B1 | 10/2001 | Kohayakawa |
| 2004/0156019 | A1 | 8/2004 | Masaki |
| 2009/0207378 | A1* | 8/2009 | Ito .................. A61B 3/0075 351/245 |
| 2013/0162946 | A1* | 6/2013 | Dobashi .................. A61B 3/14 351/206 |
| 2014/0028977 | A1 | 1/2014 | Umekawa et al. |
| 2014/0375680 | A1* | 12/2014 | Ackerman ............ G06T 19/006 345/633 |
| 2015/0313468 | A1* | 11/2015 | Okada .................. A61B 3/0083 351/208 |

FOREIGN PATENT DOCUMENTS

| | | |
|---|---|---|
| EP | 2 090 221 A1 | 8/2009 |
| EP | 2644086 A1 | 10/2013 |
| JP | S59-97644 A | 6/1984 |
| JP | H10-216089 A | 8/1998 |
| JP | H11-47094 A | 2/1999 |
| JP | 2008-054929 A | 3/2008 |
| JP | 2008-136617 A | 6/2008 |
| JP | 2013-066760 A | 4/2013 |
| WO | 00/013571 A1 | 3/2000 |

OTHER PUBLICATIONS

Nov. 8, 2017 Partial Search Report issued in European Patent Application No. 17173945.1.

\* cited by examiner

CAMERA IMAGE (NO DISTORTION) → DISTORTION CONSIDERED → CAMERA IMAGE (WITH DISTORTION)

CAMERA IMAGE (WITH DISTORTION)

OPHTHALMIC APPARATUS

CROSS-REFERENCE TO RELATED APPLICATIONS

This application is based upon and claims the benefit of priorities from the prior Japanese Patent Applications No. 2016-112274, filed Jun. 3, 2016, No. 2016-112275, filed Jun. 3, 2016, and No. 2016-112276, filed Jun. 3, 2016, the entire contents of which are incorporated herein by reference.

BACKGROUND

Technical Field

The present disclosure relates to an ophthalmic apparatus for examining an examinee's eye and a non-transitory storage medium storing an ophthalmic apparatus control program.

Background

Conventional ophthalmic apparatuses have been known as eye refractive power measuring apparatuses, corneal curvature measuring apparatuses, intraocular pressure measuring apparatuses, fundus cameras, OCTs, SLOs, and others, for example. Each of these apparatuses is usually configured such that an operation member such as a joystick is operated to move an optometric part in each of an up and down direction, a left and right direction, and a back and forth direction with respect to an examinee's eye to align the optometric part with the examinee's eye in a predetermined position. When the examinee's eye is positioned out of a movable range of the optometric part, an examiner operates a jaw rest and others supporting an examinee's jaw so that the examinee's eye is placed within the movable range of the optometric part (see Patent Literature 1).

Further, in the conventional ophthalmic apparatuses, there has been proposed an apparatus for aligning the optometric part with respect to the examinee's eye based on a photographed image of an examinee's face. In this type of apparatuses, there has been specifically proposed an apparatus for displaying an image of the examinee's face on a display part to confirm whether or not an eye level (a height of an eye) of the examinee is positioned appropriately (see Patent Literature 2).

RELATED ART DOCUMENTS

Patent Documents

Patent Literature 1: JP2008-054929A
Patent Literature 2: JP2008-136617A

SUMMARY

Technical Problems

However, in the conventional apparatuses, when the jaw rest is being adjusted its height, the examinee sometimes gets surprised at movement of the jaw rest.

The present disclosure has been made in view of the above problem and has a purpose of solving the problem by providing an ophthalmic apparatus and a non-transitory storage medium storing an ophthalmic apparatus control program that can remove an examinee's anxiety.

Means of Solving the Problems

To address the above problem, the present disclosure provides the following configuration.

There is provided an ophthalmic apparatus for examining an examinee's eye comprising: a face support part configured to support an examinee's face; a human detection part configured to detect whether the face is supported by the face support part; a notification part configured to give an announcement to any one of an examinee and an examiner; and a controller configured to control the notification part based on a detection result of the human detection part.

DETAILED DESCRIPTION OF THE EXEMPLARY EMBODIMENTS

First Embodiment

Figure 1:
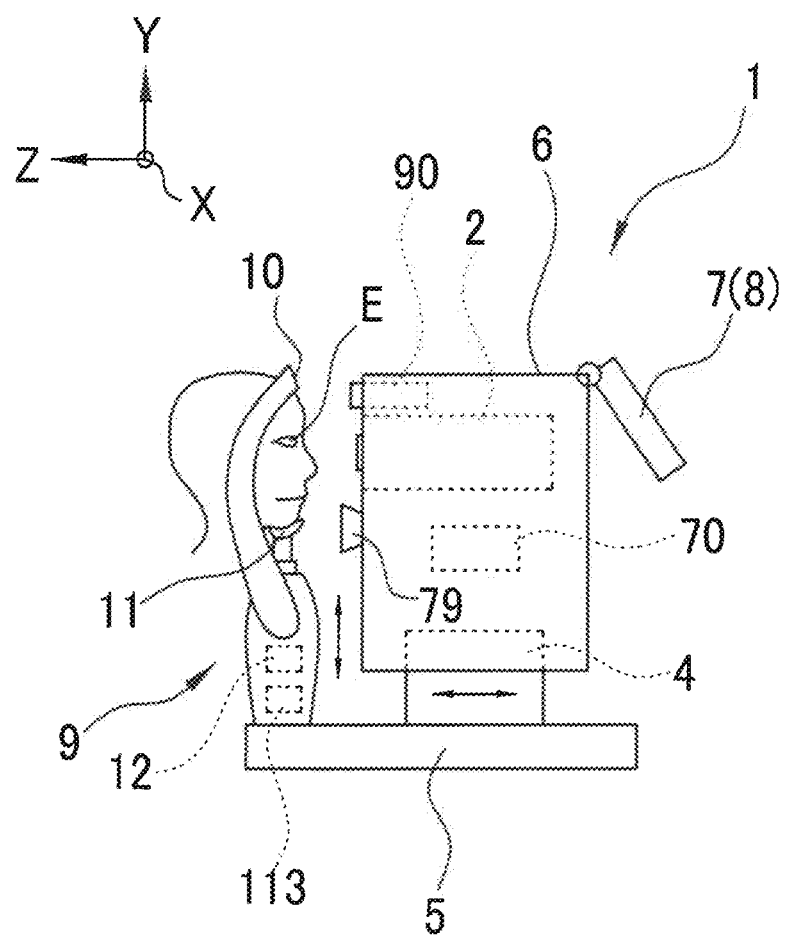
FIG. 1 is an external schematic view of the present example.

An embodiment of an ophthalmic apparatus according to the present disclosure is explained. The ophthalmic apparatus in the first embodiment examines an examinee's eye, for example. The ophthalmic apparatus may be an apparatus such as an eye refractive power measuring apparatus, a corneal curvature measuring apparatus, a corneal shape measuring apparatus, an intraocular pressure measuring apparatus, an axial length measuring apparatus, a fundus camera, an OCT, an SLO, and an ultrasonic ophthalmoscopic apparatus.

The ophthalmic apparatus is provided with an optometric part, a face photographing part, an adjustment part, and a controller, for example. The optometric part may be provided with an examination optical system, an ultrasonic measurement system, and others. The face photographing part photographs an examinee's face. The face photographing part obtains, for example, a face image including at least one of the examinee's eyes.

The adjustment part adjusts relative positions of the examinee's eye and the optometric part at least in one direction. Alternatively, adjustment may be made three-dimensionally. Specifically, the adjustment part brings the optometric part to move in a left and right (X) direction, in an up and down (Y) direction, and in a back and forth (Z) direction with respect to the examinee's eye. The adjustment part includes a driving part, for example. As another example, the adjustment part may move the examinee's eye relative to the optometric part. In this case, the adjustment part may move a face support part (such as a forehead support and a jaw rest). When the face support part includes the jaw rest, the driving part may move the jaw rest in the up and down direction.

The controller takes control of the ophthalmic apparatus. Specifically, the controller takes control of driving the driving part of the adjustment part. Further, the controller may function as an arithmetic controller for controlling an arithmetic operation of image processing and others.

The controller estimates a three-dimensional coordinate of the examinee's eye. For example, the controller assumes at least one coordinate component of the three-dimensional coordinate of the examinee's eye. To be more specific, the controller reads out a predetermined value from a memory part or the like and determines the predetermined value as a value of the coordinate component. At least one coordinate component of the three-dimensional coordinate indicates at least one of three elements of the three-dimensional coordinate. Namely, any one of an x-coordinate, a y-coordinate, and a z-coordinate may be the one coordinate component. The controller assumes that at least one coordinate component of the three-dimensional coordinate is located in a standard position, for example.

Subsequently, the controller obtains a two-dimensional coordinate on an image of the examinee's eye from a face image. The controller may detect the examinee's eye from the face image and obtain the two-dimensional coordinate of the examinee's eye from a pixel position of the thus detected examinee's eye.

The controller then calculates a temporary three-dimensional coordinate of the examinee's eye based on the one assumed coordinate component and the two-dimensional coordinate on the image of the examinee's eye which is detected from the face image. The controller then controls the driving part based on the temporary three-dimensional coordinate of the examinee's eye.

As mentioned above, the ophthalmic apparatus of the first embodiment is configured to estimate the three-dimensional coordinate of the examinee's eye by a method such that the controller assumes at least one coordinate component of the three-dimensional coordinate and calculates the other coordinate components by the two-dimensional coordinate obtained by the face image of the examinee's eye and the assumed coordinate component. Accordingly, the ophthalmic apparatus of the present embodiment is enabled to make a smooth alignment based on the estimated three-dimensional coordinate even when the examinee's eye and the optometric part are placed apart.

As another example, the controller may estimate the three-dimensional coordinate of the examinee's eye by assuming a plurality of coordinate components of the three-dimensional coordinate as reference positions. For example, the controller may assume that the x-coordinate and the z-coordinate of the three-dimensional coordinate are in the reference positions and estimate the three-dimensional coordinate of the examinee's eye from the assumed x-coordinate and the assumed z-coordinate and the y-coordinate of the examinee's eye that is detected from the face image.

When the controller assumes one coordinate component, a standard z-coordinate of the examinee's eye may be assumed as one coordinate component of the three-dimensional coordinate. To be specific, while the examinee's face is supported by the face support part, a reference value of the average z-coordinate of an eye is assumed as the z-coordinate. In general, differences in the z-coordinate among individuals, the differences including whether an eyeball protrudes or is depressed relative to a forehead, are smaller than differences in a pupil distance (the x-coordinate) or a height of the eye (the y-coordinate) among individuals. Accordingly, an assumption that the z-coordinate has less differences among individual examinees makes it possible to estimate the temporary three-dimensional coordinate with less errors from an actual three-dimensional coordinate of the examinee's eye.

The controller may change conditions for coordinate components and calculate the temporary three-dimensional coordinate for several times. For example, the controller may assume the coordinate components by use of not only the reference value but also a plurality of values around the reference value. In this case, even when the alignment cannot be made in success as a result of driving the adjustment part based on one temporary three-dimensional coordinate, the ophthalmic apparatus can retry the alignment based on another temporary three-dimensional coordinate.

Furthermore, the controller may calculate a temporary three-dimensional coordinate in each case of assuming the x-coordinate, assuming the y-coordinate, and assuming the z-coordinate. In this case, the controller may control the driving part based on one of the calculated temporary three-dimensional coordinates in each of the above cases to perform the alignment of the optometric part. The ophthalmic apparatus of the present embodiment can thus obtain the further possible three-dimensional coordinate of the examinee's eye by assuming each of the x-coordinate, the y-coordinate, and the z-coordinate.

Moreover, the controller may determine whether or not the examinee's eye is positioned within the movable range of the optometric part based on the temporary three-dimensional coordinate. When the examinee's eye is out of the movable range of the optometric part, the controller may drive the face support part such that the examinee's eye is placed within the movable range of the optometric part. Thus, a test can be performed even if the examinee's eye is out of the movable range of the optometric part.

The ophthalmic apparatus may further be provided with an alignment detection part. The alignment detection part detects an alignment state of the examinee's eye and the optometric part, for example. The alignment detection part is provided with an anterior segment photographing optical system and a target projecting optical system, for example.

The anterior segment photographing optical system photographs an anterior segment of the examinee's eye. The target projecting optical system projects an alignment target on the examinee's eye. Specifically, the alignment detection part detects the alignment target from an anterior segment image and then detects the alignment state from a position of the alignment target.

When the controller drives the driving part based on the temporary three-dimensional coordinate, detection of the alignment state by the alignment detection part may be performed in parallel. Further, when the alignment state is detected before the optometric part reaches a position of the temporary three-dimensional coordinate, the optometric part may be driven based on the alignment state detected by the alignment detection part. Accordingly, the alignment can be transited from a rough alignment based on the temporary three-dimensional coordinate to a fine alignment based on a detection result of the alignment detection part.

The controller may determine whether or not the examinee's face is inclined based on the temporary three-dimensional coordinates of both eyes. To be specific, the controller may determine that the examinee's face is inclined when the three-dimensional coordinates of both eyes are largely different from each other in the up and down direction. The controller performs error processing when the examinee's face is determined to be inclined. The error processing includes suspension of measurement and notification of urging the examinee to confirm the way of placing the face, for example. To be more specific, the controller may notify the examiner or the examinee that the examinee's face is inclined by a notification part such as a display part, a speaker, a light source. By correcting the inclination of the examinee's face as mentioned above, it is possible to prevent deviation in the measured value of an astigmatic axial angle or the like.

Further, on receiving an output signal from a jaw rest driving button, the controller may drive the jaw rest to a position calculated based on a temporary three-dimensional position. The jaw rest driving button may be, for example, provided in an apparatus body, displayed on the display part, or provided in an external device connected to the apparatus body. When the temporary three-dimensional position of the examinee's eye is located upper than the movable range of the optometric part, the controller determines a driving direction to move the jaw rest as a downward direction. On the contrary, when the temporary three-dimensional position is located lower than the movable range of the optometric part, the controller determines the driving direction to move the jaw rest as an upward direction. The controller can thus determine a direction to move the jaw rest based on the temporary three-dimensional position of the examinee's eye, and therefore, there is no need for the examinee to pay attention to the driving direction of the jaw rest. Furthermore, not only the driving direction but also a driving amount of moving the jaw rest can be obtained based on the temporary three-dimensional position, and accordingly, the controller can automatically move the jaw rest in an appropriate position. Moreover, one driving button is enough for moving the jaw rest in the both up and down directions, and thus there is no need to provide two buttons consisting one button for moving the jaw rest upward and the other one for moving the jaw rest downward, thus simplifying the apparatus configuration. Even in a case of providing two buttons, the controller may be configured to invalidate an input from one button directed to a direction different from the driving direction of the jaw rest, the driving direction having been determined based on the temporary three-dimensional position of the examinee's eye, and the controller may further be configured to move the jaw rest in the driving direction calculated by the controller even when any one of the buttons is pressed.

The controller may wait for an output of the jaw rest driving button even if it is determined that the jaw rest needs to be moved. After the controller receives the output from the jaw rest driving button, the controller may automatically drive the jaw rest so that the temporary three-dimensional position of the examinee's eye enters in the driving range of the optometric part. Thus, there is no possibility of causing sudden movement of the jaw rest.

Further, the controller may drive the jaw rest only when the output from the jaw rest button is continuously received. Specifically, the controller may drive the jaw rest only when the jaw rest button is being pressed, and when the jaw rest driving button is no longer pressed, the controller may cease moving the jaw rest. Thus, the examiner is able to stop moving the jaw rest only by releasing the jaw rest driving button in a case that the examinee's face is about to get caught between the jaw rest and the forehead support.

Further, the controller may cease driving the jaw rest while the examinee's face is supported by the face support part. Specifically, while a sensor is detecting a state in which the examinee's face is on the face support part, the controller may not move the jaw rest. To be more specific, while a sensor provided in the jaw rest is detecting that the examince's face is placed on the jaw rest, the controller may cease moving the jaw rest, and the controller may move the jaw rest when the sensor detects that the examince's face is apart from the jaw rest. Thus, it is possible to prevent the examinee's face from getting caught in a clearance of the apparatus due to movement of the jaw rest. When a driving amount of moving the jaw rest is less than a predetermined value (for example, 5 mm), the jaw rest may be move irrespective of a detection result of the sensor. Furthermore, detection of the examinee's face on the face support part may be determined by detection of the examinee's eye on the face image that is photographed by the face photographing part.

The face photographing part may be either a non-telecentric optical system or a telecentric optical system. When the face photographing part is the telecentric optical system, the controller may offset each displacement amount in X and Y directions of an examining optical axis of an examining member and a photographing optical axis of the face photographing part to perform alignment by the face image.

Second Embodiment

A second embodiment is explained. The ophthalmic apparatus of the second embodiment is, for example, configured to give an announcement to an examinee or an examiner when an examinee's eye is about to be examined. The ophthalmic apparatus (for example, an ophthalmic apparatus 1) is mainly provided with a human detection part (for example, a face photographing part 90, a sensor 113, and others), a notification part (for example, a speaker 79), and a controller (for example, a controller 70).

The human detection part specifically detects presence or absence of the examinee. The human detection part is, more specifically, configured to detect whether or not the examinee makes his/her face supported by the face support part. The human detection part may be a jaw rest sensor provided in the jaw rest, for example. The jaw rest sensor is, specifically, a sensor for detecting that an examinee's jaw is placed on the jaw rest. The detected result of the human detection part is input in the controller.

The notification part gives an announcement to the examinee or the examiner, for example. The notification part may be an audio output part (such as a speaker 79). Specifically, the notification part makes an audio announcement to the examinee or the examiner. The audio announcement includes announcements such as "please leave the jaw," "please blink an eye," and "please open your eye widely." The notification part may display a message on the display part or turn on a display lamp to notify the examinee or the examiner.

The controller takes control of each part such as the notification part of the ophthalmic apparatus. For example, the controller determines the presence or the absence of the examinee based on the detected result of the human detection part. The controller also controls the notification part. The controller may control the notification part based on a determination result of the presence or the absence of the examinee.

The apparatus of the second embodiment is configured to control the notification part based on the detected result of the human detection part to make an appropriate announcement according to an examinee's state. Therefore, even when the examiner is away from the examinee or the apparatus, the examinee can easily take a test by following the announcements by the ophthalmic apparatus.

The ophthalmic apparatus may be, for example, provided with a jaw rest (jaw rest 11) and a jaw rest driving part (jaw rest driving part 12). The jaw rest specifically supports an examinee's jaw. The jaw rest driving part drives the jaw rest in an up and down direction to adjust the height of the jaw rest. When the ophthalmic apparatus is provided with the jaw rest and the jaw rest driving part, the controller may control the notification part to give an announcement to ask the examinee to leave the jaw from the jaw rest. At this time, the controller determines the presence or the absence of the examinee from the detected result of the human detection part, and when the examinee is determined to be present, the controller may make an announcement of asking the examinee to leave the jaw from the jaw rest. When the examinee has left the jaw rest and the human detection part does not detect the presence of the examinee, the controller drives the jaw rest.

Further, the controller may change contents of the announcement according to a driving amount to move the jaw rest to an appropriate position. For example, when the driving amount of the jaw rest is larger than a predetermined amount, the controller may give the announcement to ask the examinee to leave the jaw from the jaw rest. When the driving amount is smaller than the predetermined amount, the controller may give the announcement of driving the jaw rest while the examinee's jaw is kept placed on the jaw rest. Accordingly, the controller may determine whether or not to make the announcement of asking the examinee to leave the jaw from the jaw rest based on the amount of the driving amount. As a result of this, when the jaw rest has only to be adjusted a little, a test can be carried out without especially making the examinee leave the jaw from the jaw rest.

The human detection part may be configured with a face photographing part and the controller, for example. The face photographing part specifically photographs a face image including at least one of the examinee's left and right eyes. The controller may determine the examinee to be absent when the examinee's eye is not detected from an image photographed by the face photographing part, and the controller may determine the examinee to be present when the examinee's eye is detected.

After the test for the examinee has ended, the controller may give an announcement of initialization before actually initializing at least one of the optometric part and the jaw rest. To be specific, the controller gives an announcement of "initialization will be performed" after the test for the examinee has ended, and then returns the optometric part, the jaw rest, and others to their initial positions. Thus, the examinee or the examiner can be prevented from striking the apparatus and getting surprised at an initialization operation.

The controller may make a further announcement of urging the examinee to blink. Specifically, the controller may control the notification part to output a sound such as "please blink an eye." The ophthalmic apparatus may further include a blink detection part. The blink detection part may detect the blink by image-processing an image photographed by an anterior segment camera or the like. The controller may, for example, start testing the examinee's eye after the blink of the examinee's eye is detected by the blink detection part.

Third Embodiment

A third embodiment is now explained. An ophthalmic apparatus of the third embodiment is, for example, provided with a controller (an arithmetic controller). The controller sets a region of interest (ROT) on an image photographed by the face photographing part and processes an image signal in the set ROI. The controller may set the ROI for detecting at least a part of the examinee's face, and more specifically, set the ROI for detecting the examinee's eye or set the ROI for detecting at least a part of the skin of the examinee's face. In those examples, there is a case that an arbitrary part of the entire face is set as the ROT, and another case is that a predetermined part (such as an eye) of the entire face is set as the ROI.

The controller may detect the examinee's eye by processing the image signal in the ROI or may obtain an evaluation value for controlling a photographing condition of the face photographing part by processing the image signal in the ROI. The evaluation value in this example may be the one for evaluating a luminance of the examinee's face.

The controller may control the apparatus based on the image signal in the ROI, for example. In this case, the controller may control the photographing condition of the face photographing part based on the image signal in the ROI, or may control movement of the optometric part moved by the adjustment part based on the image signal in the ROI. Controlling the photographing condition includes, for example, an automatic gain control of the face photographing part and an automatic exposure time control. Furthermore, the controller may control the photographing condition of the face photographing part based on the image signal in the ROI, and then control movement of the optometric part moved by the adjustment part based on the photographed image obtained under the controlled photographing condition. Moreover, the controller may automatically control an illumination condition of a face illumination optical system based on the image signal in the ROI.

For setting the ROI, the controller may set the ROI on the photographed image based on the position of the optometric part which is moved by the adjustment part. In this case, a position of the ROI on the photographed image corresponding to the position of the optometric part may be stored in advance in a memory part, and the controller may set the ROI based on the position of the ROI which has been stored in advance in the memory part. In this example, the ROI may be set on the photographed image based on a positional relation between the optometric part and the examinee supported by the face support part.

Setting the ROI based on the position of the optometric part enables to easily specify at least a part of the examinee's face, and thus it is possible to smoothly carry out processing of the image signal of at least a part of the face. When at least a part of the face is detected based on the photographed image of the face photographing part, there is a case that it becomes difficult to perform the detection due to influence of noise shot or the like. To address this, at least a part of the face can be easily detected by processing the image signal in the ROI which is set according to the positional relation of the optometric part and the examinee.

To be more specific, the controller controls the photographing condition for the face photographing part based on the image signal in the ROI which is specified by image processing, and then processes the photographed image obtained after controlling the photographing condition to detect the examinee's eye. Thus, for example, the eye can be detected in a state in which a contrast between the skin and the eye of the examinee is adjusted. In this case, the ROI may be set on at least a part of the examinee's entire face or a part of the examinee's skin. At least a part of the examinee's face may be specified by use of a luminance difference between the examinee's face and a background, a pattern matching, and others.

<Positional Change in Region of Interest According to Position of Optometric Part>

When the region of interest (ROI) is to be set based on the position of the optometric part, for example, the controller may change the position of the ROI on the photographed image according to positional changes of the optometric part. Thereby, at least a part of the examinee's face can be surely detected even when the positional relation of the examinee's face and the optometric part is changed due to changes in the position of the optometric part.

The controller may obtain positional information of the optometric part based on the detected signal from a position detection sensor that is configured to detect the position of the optometric part and set the ROI corresponding to the obtained positional information. The position detection sensor has various variations including a potentiometer provided on a base movably holding the optometric part and an encoder provided in a motor section of the driving part.

When the ROI is changed its position according to the position of the optometric part, for example, the controller may shift the ROI on the photographed image in the left and right direction in accordance with the positional change of the optometric part in the left and right direction. Thereby, even when the optometric part is moved rightward or leftward, at least a part of the face can be smoothly detected.

The controller may further be configured to shift the ROI on the photographed image according to changes in the three-dimensional position of the optometric part. Thereby, even when the optometric part is moved three-dimensionally, at least a part of the face can be smoothly detected.

<Automatic Gain Control>

When the controller is to control the photographing condition of the face photographing part based on the image signal on the ROI, the controller may carry out automatic gain control for the face photographing part based on the image signal in the ROI. The automatic gain control is carried out based on the image signal in the ROI which has been set based on the position of the optometric part, so that the luminance of the face image is adjusted to be in an allowable level. Accordingly, even if there is influence of ambient light and others, the face position is specified, and the contrast between the face and the eye of the examinee is adjusted. Consequently, the eye detection on the photographed image can be surely performed, enabling smooth alignment with the examinee's eye.

The controller may set the ROI corresponding to the position of the optometric part so that an image region including at least a part of the skin of the face is set as the ROI to accurately adjust the contrast between the skin of the examinee's face and the examinee's eye. Further, the controller may set the ROI corresponding to the position of the optometric part so that the ROI is not set other than the face image (such as the background and the hair) but is set in the image region including a center part of the examinee's face.

For the automatic gain control, the image signal in an analysis region may be analyzed and processed to obtain an evaluation value for performing the automatic gain control. The evaluation value for the automatic gain control may be an average luminance within the ROI, an accumulated luminance value of each pixel within the ROI, and the maximum luminance value within the ROI, for example. Further, the evaluation value may be a contrast of an image within the ROI, a histogram, and others.

In the above explanation, the automatic gain control of the face photographing part is performed based on the image signal in the ROI, but the above embodiment can be applied to another case of performing an automatic control of an exposure time of the face photographing part based on the image signal in the ROI.

<Detection of Eye Position>

The controller may detect the eye position on the photographed image based on the image signal in the ROI which has been set based on the position of the optometric part, for example. The position of the examinee's eye can be thus specified by utilizing the position of the optometric part, and accordingly, detection of the eye on the photographed image can be surely performed, leading to smooth alignment with the examinee's eye. A specific method of detecting the eye may include detection of a target (such as an anterior segment reflected image) formed in the eye or detection of a featured portion (such as a pupil, an iris, a sclera, and a blood vessel) of the eye. The ROI may be set as a search range for searching an eye on the photographed image.

When the optometric part is placed in a predetermined position, the controller may set the ROI corresponding to a predetermined position of the optometric part and carry out the eye detection by analyzing and processing the image signal in the ROI. Setting the ROI corresponding to the predetermined position leads to reduction in influence of the image region (such as the background and the hair), which could be a cause for noise, and thus the eye position in the face is detected.

Further, the controller may change the position of the ROI according to the position of the optometric part and carry out the eye detection by analyzing and processing the image signal in the thus changed ROI. Thereby, the influence of the image region causing noise is reduced and the eye position in the face is detected irrespective of the position of the optometric part.

The controller may carry out the automatic gain control based on the image signal in the ROI and detect the eye position based on the image signal in the ROI set on the photographed image, which has been adjusted by the automatic gain control. In this case, the ROI for detection of the eye position may be different in its position or its size with respect to the ROI for the automatic gain control. Thus, each control can be performed accurately. The configuration is not limited to the above, and the ROI with the same position and the same size can be used for the automatic gain control and the detection of the eye position.

EXAMPLES

An ophthalmic apparatus according to the present disclosure is now explained with reference to the accompanying drawings. The following explanation is given by exemplifying an eye refracting power measuring apparatus as an ophthalmic apparatus, but the present disclosure is applicable for other ophthalmic apparatuses such as a corneal curvature measuring apparatus, a corneal shape measuring apparatus, an intraocular pressure measuring apparatus, an axial length measuring apparatus, a fundus camera, an OCT (Optical Coherence Tomography), and an SLO (Scanning Laser Ophthalmoscope).

The ophthalmic apparatus of the present example objectively measures an eye refractive power of an examinee's eye, for example. The ophthalmic apparatus of the present example may be used for measuring each eye or measuring both eyes at the same time (with a binocular vision). The ophthalmic apparatus is mainly provided with an optometric part, a photographing part, a driving part, and a controller.

<External Appearance>

Referring to FIG. 1, an external appearance of the ophthalmic apparatus is explained. As shown in FIG. 1, an ophthalmic apparatus 1 of the present example is mainly provided with an optometric part 2, a face photographing part 90, and a driving part 4. The optometric part 2 examines an examinee's eye. The optometric part 2 is provided with an optical system to measure an eye refractive power, a corneal curvature, an intraocular pressure, and others of the examinee's eye, for example. Further, the optometric part 2 may be provided with an optical system or the like to photograph an anterior segment, a fundus, and others of the examinee's eye. The present example is explained with exemplifying the optometric part 2 for measuring the refractive power. The face photographing part 90 specifically photographs a face of the examinee. The face photographing part 90 photographs the face including at least one of the examinee's left and right eyes, for example. The driving part 4 specifically moves the optometric part 2 and the face photographing part 90 with respect to a base 5 in an up and down direction, a left and right direction, and a back and forth direction (in a three-dimensional direction).

The ophthalmic apparatus 1 of the present example is further provided with a housing 6, a display part 7, an operation part 8, a face support part 9, and others. Specifically, the housing 6 accommodates the optometric part 2, the face photographing part 90, the driving part 4, and others. The display part 7 specifically displays an observed image of the examinee's eye, measurement results, and others. The display part 7 may be integrally provided with the apparatus 1 or may be provided separately from the apparatus. The ophthalmic apparatus 1 is provided with the operation part 8. The operation part 8 is used for various settings of the apparatus 1 and operation at the time of starting measurement. The operation part 8 is input with various operation commands from an examiner. The operation part 8 may be a human interface such as a touch screen, a joystick, a mouse, a keyboard, a trackball, and a button. The face support part 9 is specifically provided with a forehead support 10 and a jaw rest 11. The jaw rest 11 is movable in an up and down direction by driving a jaw rest driving part 12.

<Control System>

Figure 2:
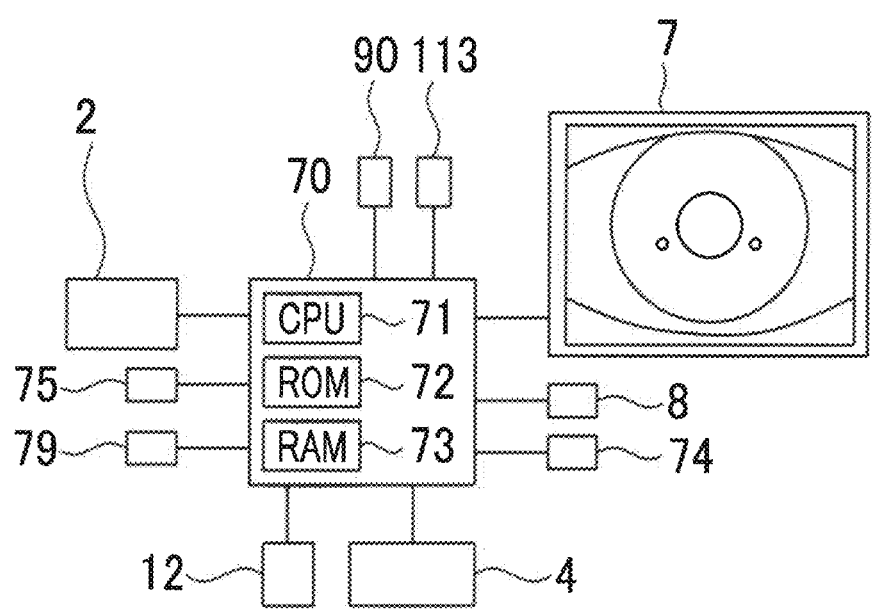
FIG. 2 is a block diagram showing a control system of the present example.

As shown in FIG. 2, the apparatus 1 includes a controller 70. The controller 70 takes charge in various control of the apparatus 1. The controller 70 is, for example, provided with a general CPU (Central Processing Unit) 71, an ROM 72, an RAM 73, and others. The ROM 72 is stored with an ophthalmic apparatus control program to control the ophthalmic apparatus, initial values, and others. The RAM temporarily stores various information. The controller 70 is connected to each of the optometric part 2, the face photographing part 90, the driving part 4, the display part 7, the operation part 8, the jaw rest driving part 12, a memory part (such as a non-volatile memory) 74, and others. The memory part 74 is, for example a non-transitory storage medium that can retain storage contents even if supply of electric source is shut off. As the memory part 74, a hard disk drive, a detachable USB flash memory or the like can be used.

<Optometric Part>

Figure 3:
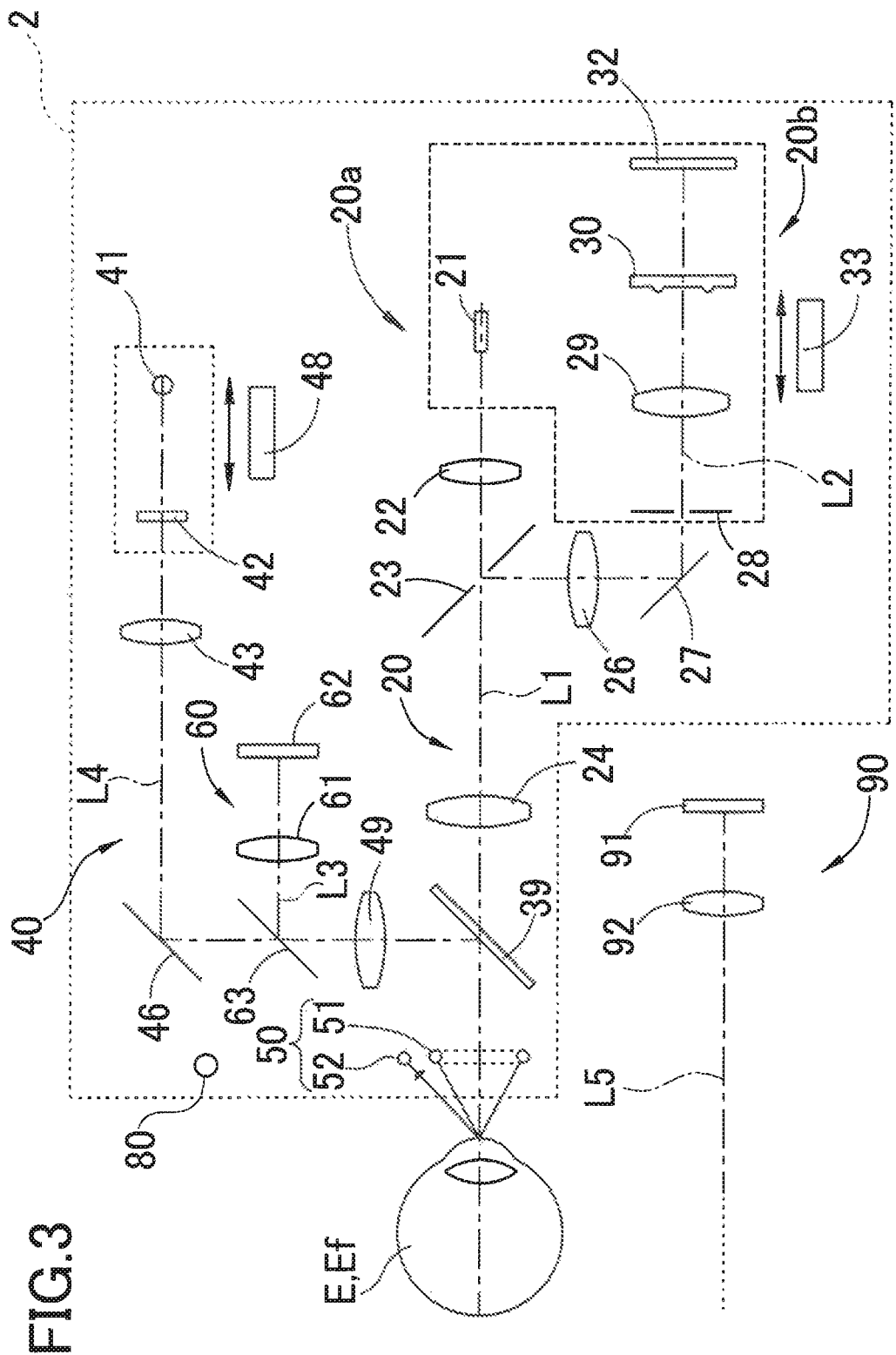
FIG. 3 is a schematic view of an optical system of the present example.

The optometric part 2 performs measurement, testing, photographing, and others for the examinee's eye. The optometric part 2 may be provided with a measuring optical system to measure a refractive power of the examinee's eye. To be specific, as shown in FIG. 3, the optometric part 2 is provided with a measurement optical system 20, a fixation target presenting optical system 40, a target projecting optical system 50, and an observation optical system (a photographing optical system) 60.

The measurement optical system 20 includes a projecting optical system 20a and a light receiving optical system 20b. The projecting optical system 20a projects a light flux on a fundus Ef through a pupil of the examinee's eye. The light receiving optical system 20b takes out a reflected light flux (fundus reflection light) in a ring-like shape from the fundus Ef through a pupil peripheral portion, and then photographs a ring-like shaped fundus reflected image which is to be mainly used for measuring the refractive power.

The projecting optical system 20a includes a measurement light source 21, a relay lens 22, a hole mirror 23, and an objective lens 24 on an optical axis L1. The light source 21 projects a spot-like light source image on the fundus Ef through the relay lens 22, the objective lens 24, and a pupil center part. The light source 21 is movable in an optical axis L1 direction by a transfer mechanism 33. The hole mirror 23 is formed with an opening to pass the light flux from the light source 21 via the relay lens 22. The hole mirror 23 is placed optically conjugate with the pupil of the examince's eye.

The light receiving optical system 20b shares the hole mirror 23 and the objective lens 24 with the projecting optical system 20a. The light receiving optical system 20b is also provided with a relay lens 26 and a total reflection mirror 27. The light receiving optical system 20b is further provided with a photo-receiving diaphragm 28, a collimator lens 29, a ring lens 30, an imaging element 32 on an optical axis L2 in a reflection direction of the hole mirror 23. The imaging element 32 may be constituted by a two-dimensional light receiving element such as an area CCD. The light receiving diaphragm 28, the collimator lens 29, the ring lens 30, and the imaging element 32 are integrally movable with the measurement light source 21 of the projecting optical system 20a in the optical axis L2 direction by the transfer mechanism 33. When the light source 21 is placed optically conjugate with the fundus Ef by the transfer mechanism 33, the light receiving diaphragm 28 and the imaging element 32 are also placed optically conjugate with the fundus Ef.

The ring lens 30 is an optical element for forming a fundus reflection light, which is introduced from the objective lens 24 via the collimator lens 29, in a ring-like shape. The ring lens 30 includes a ring-like lens part and a light shielding part. Further, when the light receiving diaphragm 28 and the imaging element 32 are placed optically conjugate with the fundus Ef, the ring lens 30 is placed optically conjugate with the pupil of the examinee's eye. The imaging element 32 is configured to receive the ring-like fundus reflection light (hereinafter, referred to a ring image) through the ring lens 30. The imaging element 32 outputs image information of the thus received ring image to the CPU 71. Thus, the CPU 71 performs display of the ring image on the display part 7, calculation of the refractive power based on the ring image, and others.

Further, as shown in FIG. 3, in the present example, a dichroic mirror 39 is placed between the objective lens 24 and the examinee's eye. The dichroic mirror 39 transmits the light emitted from the light source 21 and the fundus reflection light corresponding to the light emitted from the light source 21. The dichroic mirror 39 further introduces a light flux from the fixation target presenting optical system 40 which will be mentioned later to the examinee's eye. Furthermore, the dichroic mirror 39 reflects an anterior segment reflection light of the light emitted from the target projecting optical system 50 which will be mentioned later, and then introduces the anterior segment reflection light to the anterior segment photographing optical system 60.

As shown in FIG. 3, in front of the examinee's eye, the target projecting optical system 50 is placed. The target projecting optical system 50 mainly projects a target used for alignment of the optical systems relative to the examinee's eye on the anterior segment. To be specific, the target projecting optical system 50 projects the target used for alignment in at least any one of X and Y directions and a Z direction of the optical system relative to the examinee's eye. The alignment may be alternatively detected not by using the target projecting optical system 50 but by detecting a featured part on an anterior segment image. The alignment may be detected by both the target detection and the detection of the featured part.

The target projecting optical system 50 is specifically provided with a ring-target projecting part 51 and a target projecting part 52. The ring-target projecting part 51 projects a diffused light on the cornea of the examinee's eye E and further projects a ring target (Mayer ring). The ring-target projecting part 51 is also used for anterior-segment illumination to illuminate the anterior segment of the examinee's eye E. The target projecting part 52 projects a parallel light on the cornea of the examinee's eye and further projects an infinite light target.

The target presenting optical system 40 is provided with a light source 41, a fixation target 42, a relay lens 43 on an optical axis L4 in a reflection direction of a reflection mirror 46. The fixation target 42 is used for fixing the examinee's eye during measurement of the objective refractive power. Specifically, the fixation target 42 is illuminated with the light source 41, and thus the fixation target 42 is presented to the examinee's eye.

The light source 41 and the fixation target 42 are integrally moved in an optical axis L4 direction by a transfer mechanism 48. A presenting position (presenting distance) of the fixation target may be changed by moving the light source 41 and the fixation target 42. The examinee's eye can be thus fogged for performing the refractive power measurement.

The anterior segment photographing optical system 60 is provided with a photographing lens 61 and a photographing element 62 on an optical axis L3 in a reflection direction of a half mirror 63. The photographing element 62 is placed optically conjugate with the anterior segment of the examinee's eye. The photographing element 62 photographs the anterior segment which is illuminated by the ring-target projecting part 51. Output from the photographing element 62 is input to the CPU 71. Thus, the anterior segment image of the examinee's eye which is photographed by the photographing element 62 is displayed on the display part 7 (see FIG. 2). Further, the photographing element 62 photographs an alignment target image (in the present example, the ring target and the infinite target) that is formed on the cornea of the examinee's eye by the target projecting optical system 50. Accordingly, the CPU 71 detects the alignment target image from the thus photographed result of the photographing element 62. Further, the CPU 71 determines appropriateness of the alignment state based on a detected position of the alignment target image.

<Face Photographing Part>

The face photographing part 90 is, for example, an optical system to photograph a face including at least one of the examinee's left and right eyes. As shown in FIG. 3, the face photographing part 90 of the present example is mainly provided with a photographing element 91 and a photographing lens 92.

The face photographing part 90 of the present example is moved with the optometric part 2 by the driving part 4. As another example, the face photographing part 90 may be fixed to the base 5 and may not be movable.

The photographing lens 92 of the present example is constituted by a wide-angle lens, for example. The wide-angle lens is specifically a fisheye lens, a conical lens, or the like. Applying the wide-angle lens enables photographing of the examinee's face by the face photographing part 90 at a wide angle of field. The field angle is 87° or more, for example. Thus, the face photographing part 90 can easily photograph the examinee's both eyes.

<Control Method>

A control operation of the apparatus 1 is explained below. The apparatus 1 is configured to perform a full-automatic alignment of the optometric part 2 and the examinee's eye for testing the examinee's eye.

Figure 4:
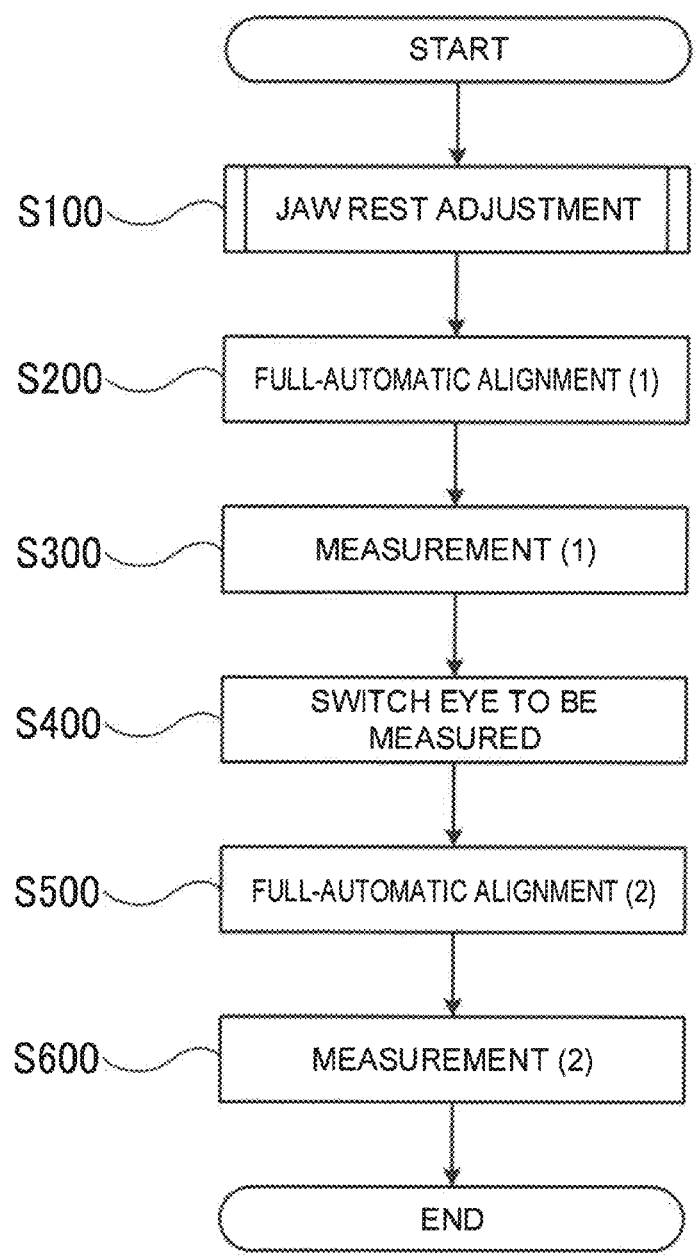
FIG. 4 is a flow chart showing an operation control of measurement in the present example.

FIG. 4 is a flow chart of a full-automatic measurement. Specifically, a controller 70 carries out measurement and then performs the full-automatic alignment to align the examinee's eye E and the optometric part 2. Subsequently, the controller 70 performs measurement of the eye and then move the optometric part 2 to the other eye for performing another full-automatic alignment. After the alignment is completed, the controller 70 measures the examinee's eye, and the process is ended. Each step of the full-automatic alignment is explained below.

(Step S100: Jaw Rest Adjustment)

In a step S100, the controller 70 performs adjustment of the jaw rest. Detailed explanation of the jaw rest adjustment will be explained below. After completing the jaw rest adjustment, the controller 70 proceeds to a step S200.

(Step S200: Full-Automatic Alignment (1))

In a step S200, the controller 70 performs the full-automatic alignment to one of the examinee's left and right eyes. Specifically, the controller 70 detects the examiner's eye from a face image photographed by the face photographing part 90 and controls the optometric part 2 to move toward the eye. At this time, the controller 70 may detect the alignment target which is projected by the target projecting optical system 50 from the anterior segment image of the examinee's eye photographed by the anterior segment photographing optical system 60. Based on information of the examinee's eye detected from the face image, the controller 70 performs the rough alignment and detects the alignment target from the anterior segment image. Subsequently, the controller 70 performs the fine alignment with the detected alignment target. To be more specific, the controller 70 moves the optometric part 2 such that the alignment target is positioned in a predetermined position to complete the alignment.

(Step S300: Measurement (1))

In a step S300, the controller 70 performs a test for the examinee's eye. Specifically, the controller 70 irradiates the measurement light on the fundus of the examinee's eye, and based on a detected result of the measurement light reflected on the fundus, the controller 70 measures the eye refractive power of the examinee's eye.

(Step S400: Switching Left and Right Eyes)

In a step S400, the controller 70 switches an eye to be measured. Specifically, the controller 70 moves the optometric part 2 from the eye that has been finished with the test in the step S300 to the other eye.

(Step S500: Full-Automatic Alignment (2))

In a step S500, the controller 70 performs the full-automatic alignment as similar to the step S200 to the examinee's eye which has not yet finished with measurement.

(Step S600: Measurement (2))

In a step S600, the controller 70 performs a test for the other one of the examinee's eyes.

<Estimation of Three-Dimensional Position>

Figure 7:
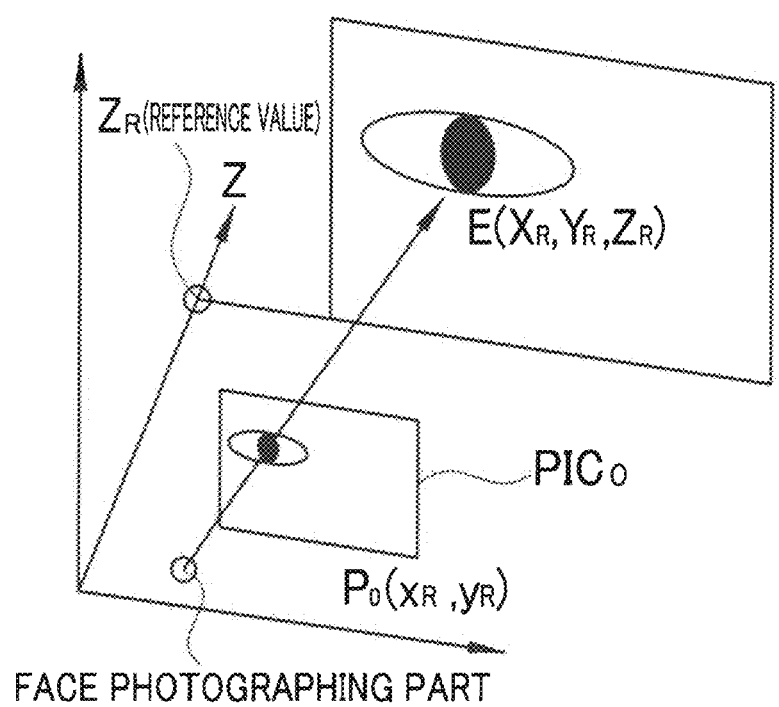
FIG. 7 is an explanatory view for explaining a three-dimensional coordinate of an examinee's eye.

A method of estimating a three-dimensional position of the examinee's eye by use of a position of the eye detected from the photographed image is now explained (see FIG. 7, for example). The following explanation is given with exemplifying a positional adjustment of the jaw rest, but the method is not limited to this and may be applied for a positional adjustment of the optometric part 2.

Figure 5:
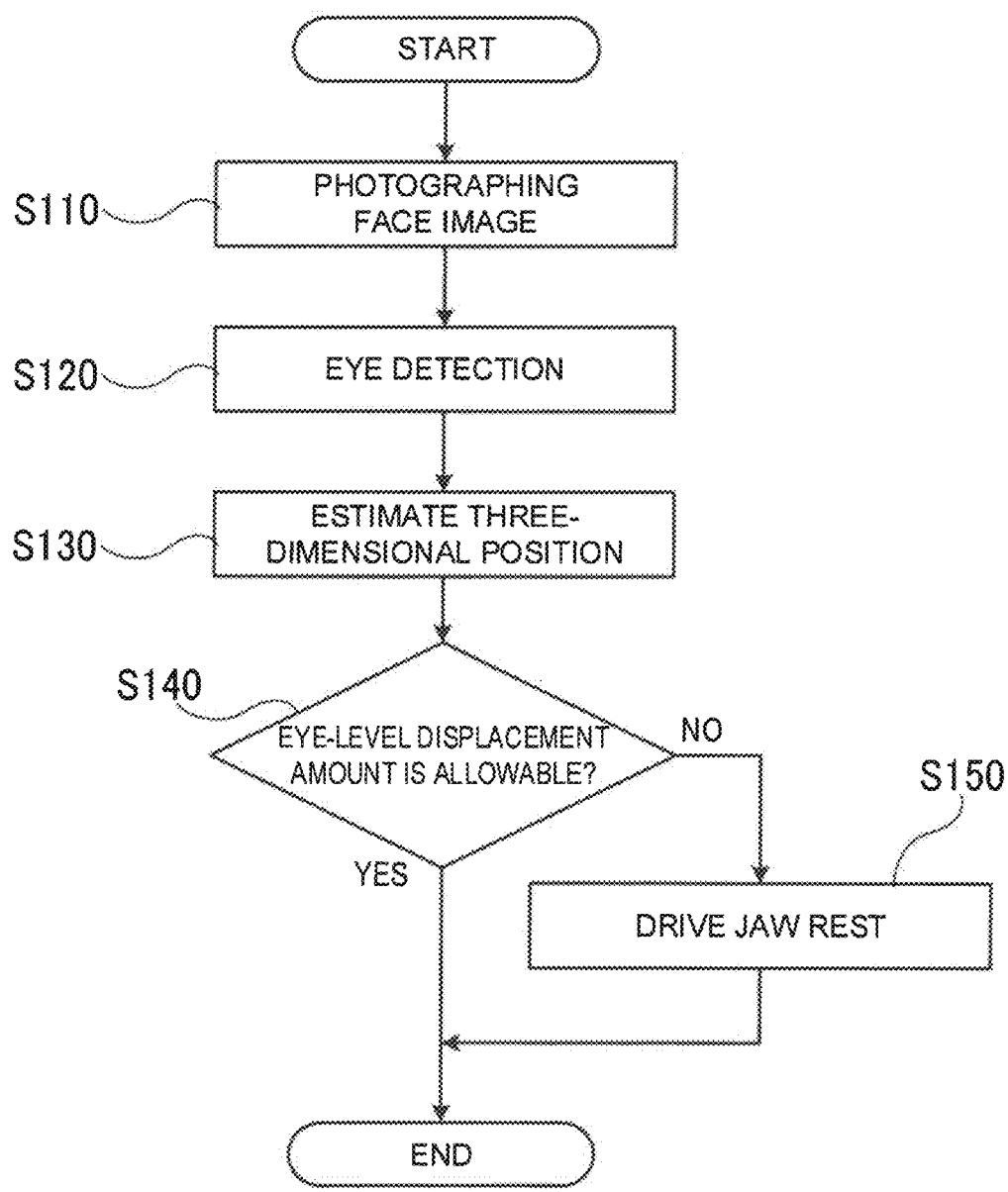
FIG. 5 is a flow chart showing an operation control of adjustment of a jaw rest in the present example.

FIG. 5 is a flow chart of controlling the jaw rest of the ophthalmic apparatus of the present example. In the present example, the controller 70 obtains a displacement amount of an eye level when the examinee places his/her face on the jaw rest 11 and then controls a height of the jaw rest 11 according to the displacement amount result.

(Step S110: Face Image Photographing)

Figure 6:
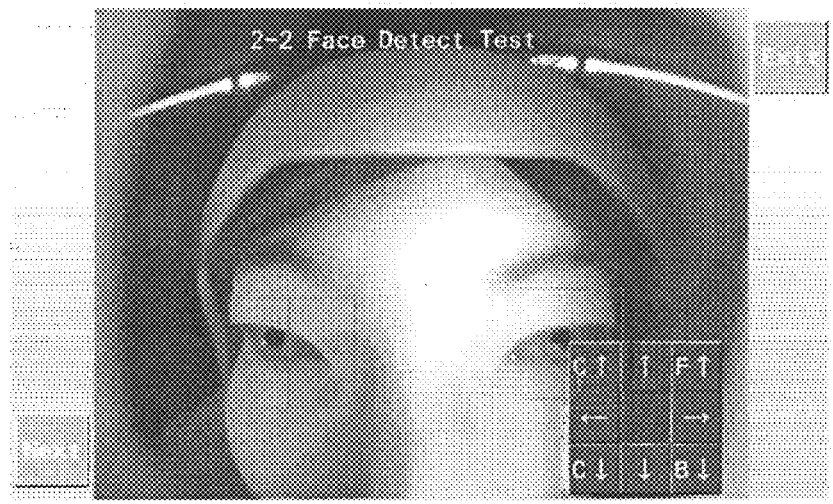
FIG. 6 is a view showing an example of a face image.

The controller 70 photographs the examinee's face in a state in which the examinee places the jaw on the jaw rest 11. FIG. 6 shows one example of the face image photographed by the face photographing part 90. The photographing position of the face photographing part 90 is roughly in a center in the left and right direction, on an eye level in the up and down direction, and in a position closer to the examiner in the back and forth direction.

(Step S120: Eye Detection)

The controller 70 detects the examinee's eye from a face image $PIC_0$ photographed in the step S110 as shown in FIG. 6, and then stores a coordinate $(x_R, y_R)$ of the examinee's right eye and a coordinate $(x_L, y_L)$ of the examinee's left eye in the memory part 74 or the like (see FIG. 7). A method of detecting the examinee's eye from the image may be various image processing methods such as detection of a pupil with infrared photographing and edge detection of a luminance value. For instance, when the examinee's face is photographed with the infrared light, the skin is imaged white and the pupil is imaged black. Accordingly, the controller 70 can detect a circled black (low in the luminance) portion of the infrared image obtained by the infrared photographing as the pupil. Utilizing the above method, the controller 70 detects the examinee's eye from the face image and obtains the two-dimensional positional information.

(Step S130: Estimation of Three-Dimensional Position)

Based on the examinee's right eye coordinate $(x_R, y_R)$ and the left eye coordinate $(x_L, y_L)$ in the image obtained in the step S120, the controller 70 calculates a three-dimensional coordinate $(X_R, Y_R, Z_R)$ of the examinee's right eye and a three-dimensional coordinate $(X_L, Y_L, Z_L)$ of the examinee's left eye. To be specific, the relation of the coordinates $(x_R, y_R)$ and $(X_R, Y_R, Z_R)$ is expressed by the following formula (1):

$$h \begin{pmatrix} x_R \\ y_R \\ 1 \end{pmatrix} = I \cdot (R | T) \cdot \begin{pmatrix} X_R \\ Y_R \\ Z_R \\ 1 \end{pmatrix} \quad (1)$$

wherein h represents a constant, I represents a camera internal parameter. When each focal length is represented as $f_x$ and $f_y$, a skew distortion is represented as s, and a coordinate of an optical center is represented as $(c_x, c_y)$, the following formula (2) is given:

$$I = \begin{pmatrix} f_x & s & c_x \\ 0 & f_y & c_y \\ 0 & 0 & 1 \end{pmatrix}. \quad (2)$$

Further, the following formulas (3) and (4) are given wherein (R|T) represents a camera external parameter, R represents a rotational component, and T represents a parallel movement component:

$$R = \begin{pmatrix} r_{11} & r_{12} & r_{13} \\ r_{21} & r_{22} & r_{23} \\ r_{31} & r_{32} & r_{33} \end{pmatrix}; \quad (3)$$

$$T = \begin{pmatrix} t_X \\ t_Y \\ t_X \end{pmatrix}. \quad (4)$$

In the formula (1), when $(x_R, y_R)$, I, R, and T are known values, h, $(X_R, Y_R, Z_R)$ are unknown values. Assuming that one of these four unknown values is a reference value, there are three unknown values h, $X_R, Y_R$, and thus these unknown values can be obtained by solving the above formula (1).

In a state in which the face is placed on the jaw rest 11, the Z-coordinate of the eye is mostly in the same position, and differences among individuals are considered not to be so large as compared with a left and right position (i.e., PD) and an up and down position (which depends on a size of the face, a position of the jaw rest, or the like). Accordingly, in the present example, $Z_R$ is assumed to be the reference value. The formula (1) is developed as the following formula (5):

$$h \begin{pmatrix} x_R \\ y_R \\ 1 \end{pmatrix} = I \cdot R \cdot \begin{pmatrix} X_R \\ Y_R \\ Z_R \end{pmatrix} + I \cdot T. \quad (5)$$

The following formula (6) is also given:

$$hR^{-1} \cdot I^{-1} \cdot \begin{pmatrix} x_R \\ y_R \\ 1 \end{pmatrix} = R^{-1} \cdot I^{-1} \cdot I \cdot R \cdot \begin{pmatrix} X_R \\ Y_R \\ Z_R \end{pmatrix} + R^{-1} \cdot I^{-1} \cdot I \cdot T \quad (6)$$

$$hR^{-1} \cdot I^{-1} \cdot \begin{pmatrix} x_R \\ y_R \\ 1 \end{pmatrix} = \begin{pmatrix} X_R \\ Y_R \\ Z_R \end{pmatrix} + R^{-1} \cdot T.$$

Further, there provides matrix M and N which are expressed by the following formulas (7) and (8):

$$M = \begin{pmatrix} m_1 \\ m_2 \\ m_3 \end{pmatrix} = R^{-1} \cdot I^{-1} \cdot \begin{pmatrix} x_R \\ y_R \\ 1 \end{pmatrix}; \quad (7)$$

$$N = \begin{pmatrix} n_1 \\ n_2 \\ n_3 \end{pmatrix} = R^{-1} \cdot T. \quad (8)$$

With the matrix M and N, the formula (6) is further developed as the following formula (9):

$$h \begin{pmatrix} m_1 \\ m_2 \\ m_3 \end{pmatrix} = \begin{pmatrix} X_R \\ Y_R \\ Z_R \end{pmatrix} + \begin{pmatrix} n_1 \\ n_2 \\ n_3 \end{pmatrix}. \quad (9)$$

From the formula (9), h is obtained by the following formula (10):

$$h = \frac{Z_R + n_3}{m_3}. \quad (10)$$

Accordingly, with the formulas (9) and (10), $X_R$ and $Y_R$ are obtained by the following formula (11):

$$\begin{cases} X_R = \dfrac{Z_R + n_3}{m_3} m_1 - n_1 \\ Y_R = \dfrac{Z_R + n_3}{m_3} m_2 - n_2 \end{cases} \quad (11)$$

The controller 70 thus obtains $X_R$ and $Y_R$ by the formula (11). The reference value of $Z_R$ may be set as an average eye position at the time when the examinee places his/her face on the face support part 9, for example. The reference value of $Z_R$ may be stored in the memory part 74 or the like so that the examiner can freely change the value. Similarly, the controller 70 derives $X_L$ and $Y_L$.

(Step S140: Determination of Displacement Amount of Eye Level)

The controller 70 performs calculation of a displacement amount displaced from an appropriate eye level of the examinee's eye. Specifically, the controller 70 calculates a displacement amount of the three-dimensional coordinate of the examinee's eye calculated in the step S130 displaced from the appropriate eye level. Either one of the coordinate $Y_R$ or $Y_L$ obtained in the step S130 that has larger error in the displacement amount is determined to be the eye-level displacement amount. When the eye-level displacement amount is certainly within an allowable range, the controller 70 determines the eye level as measurable and then terminates the jaw rest adjustment.

For example, on condition that a movable range of moving the optometric part 2 in the Y direction and measuring the examinee's eye is in a range of +α to −α, the eye level is determined to be measurable when the estimated height of the examinee's eye is within a range of +β to −β which is a narrower range than the movable range of +α to −α. The estimated position of the examinee's eye has a gap, and thus the controller 70 performs the determination with the range of +β to −β which is the narrower range than the movable range of +α to −α so that the controller 70 determines the measurable eye level only when the examinee's eye is within the surely measurable movable range.

Figure 8A:
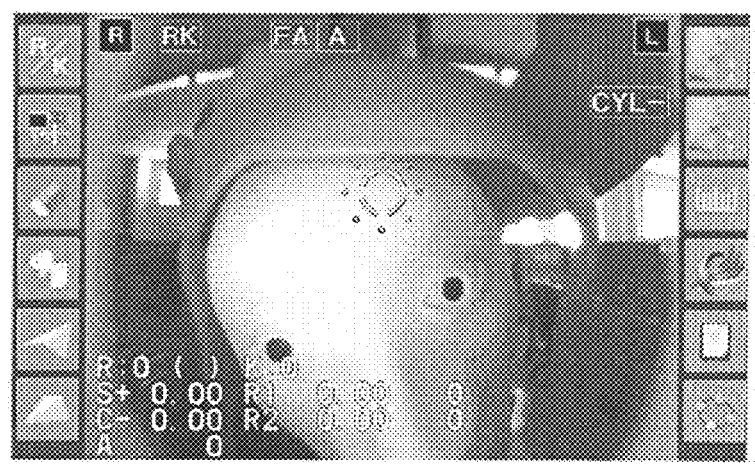
FIG. 8A is a view showing an example of the face image when an examinee's face is inclined.
Figure 8B:
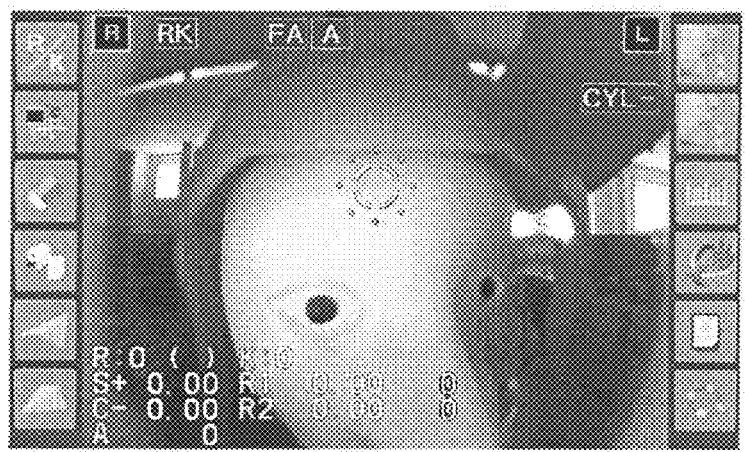
FIG. 8B is a view showing another example of the face image when the examinee's face is inclined.
Figure 9:
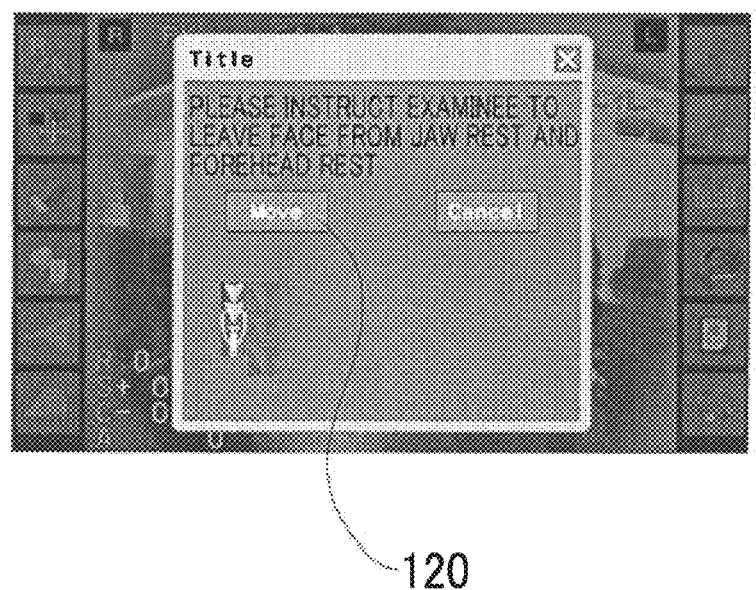
FIG. 9 is a view showing an example of a jaw rest button.
Figure 10:
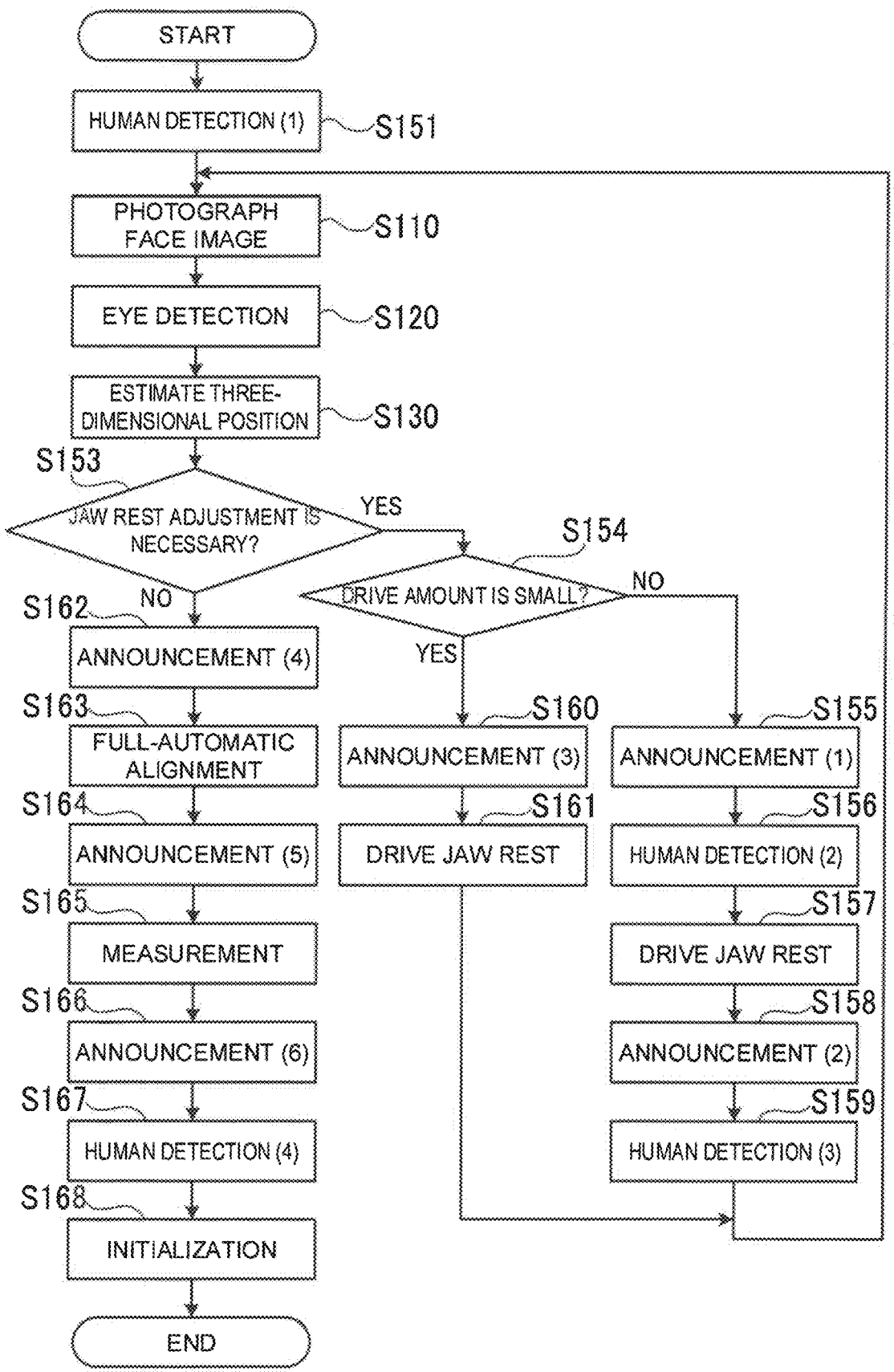
FIG. 10 is a flow chart for explaining an audio announcement.

When the face is considered to be inclined from the result of estimating the three-dimensional coordinate, the controller 70 may conclude the result as being an error. For example, when the examinee's face is inclined as shown in FIG. 8A, the difference between the estimated $Y_R$ and $Y_L$ becomes large, thus the result is concluded as error. Further, when the face is oriented in an axial direction about a Y-axis, the difference between the actual Z-coordinate and the reference position $Z_R=Z_L$ becomes large, and accordingly, the difference between the estimated $Y_R$ and $Y_L$ becomes large. When the difference between $Y_R$ and $Y_L$ is large, the controller 70 concludes the result as error since the face is oriented inappropriately.

(Step S150: Jaw Rest Driving)

In the step S140, when the appropriate eye level is determined to be large, the controller 70 drives the jaw rest 11 by the displacement amount. For example, the controller 70 controls the display part 7 to display a message of asking the examinee to leave the face from the forehead support 10 and the jaw rest 11. To be more specific, the examiner asks the examinee to leave the face from the jaw rest 11 and presses the jaw rest button 120. When the jaw rest button 120 is pressed, the controller 70 drives the jaw rest 11 to a target position based on the calculated displacement amount. The controller 70 thus drives the jaw rest 11 such that the eye level of the examinee is positioned within the movable range of the optometric part 2.

One coordinate component of the three-dimensional coordinate is assumed as mentioned above, and thereby the three-dimensional position of the examinee's eye can be estimated by an image photographed at one position by one face photographing part 90. Accordingly, the controller 70 can calculate an adjustment amount of the jaw rest for moving the examinee's eye to a measurable eye level.

Further, the controller 70 obtains information of a direction to move the jaw rest 11, and thus the examiner does not have to specify the direction to move the jaw rest 11. Furthermore, there is no need for the examiner to confirm whether the height of the jaw rest 11 is appropriate by looking and to move the jaw rest 11 upward or downward. The examiner only has to press the jaw rest button 120.

It is further possible to easily obtain a jaw rest adjustment amount without performing a stereoscopic analysis, thereby suppressing cost increase caused by providing a plurality of cameras and reducing the measurement time required for photographing from a plurality of positions. Moreover, it is not necessarily required to provide a special camera such as the telecentric optical system.

In the step S150 of the jaw rest adjustment, the controller 70 may move the jaw rest only while the jaw rest button 120 is being pressed, and the controller 70 may stop moving the jaw rest when the jaw rest button 120 is released. In this case, the controller 70 drives the jaw rest 11 based on the calculated displacement amount, and when the jaw rest reaches the target position, the controller 70 terminates the jaw rest adjustment while the jaw rest button 120 is being pressed.

In the step S150, the controller 70 may detect that the examinee's face has left the jaw rest 11 based on a sensor provided in the jaw rest or an eye detection result of the face image photographed by the face photographing part, and then automatically move the jaw rest 11 to the target position. Alternatively, the controller 70 may automatically move the jaw rest 11 by the eye-level displacement amount irrespective of the presence or the absence of the examinee.

The above controls may be combined. Specifically, when the eye-level displacement amount is small, the controller 70 moves the jaw rest 11 to the target position by pressing the jaw rest button 120, and when the eye-level displacement amount is large, the controller 70 moves the jaw rest 11 to the target position at the timing when it is detected that the examinee's face has left the jaw rest 11.

In the above explanation, the controller 70 detects both eyes from the face image and estimates the three-dimensional positions of the both eyes. Alternatively, driving of the jaw rest or the optometric part may be performed by estimating the three-dimensional position of only one eye.

In the present example, the height of the jaw rest 11 is controlled based on the estimated three-dimensional coordinate, but alternatively, the estimated value of the three-dimensional coordinate may be used for positional controlling of the optometric part 2. For example, the controller 70 may move the optometric part 2 based on a temporary three-dimensional coordinate to perform the rough alignment, and further perform the alignment detection with the alignment target of the anterior segment image. Subsequently, the controller 70 may perform the fine alignment based on the alignment target after the alignment target is detected. The controller 70 may further move the optometric part 2 based on the temporary three-dimensional coordinate even when the examinee's eye exists within the driving range of the optometric part 2 and there is no need to move the jaw rest 11.

The controller 70 may estimate the x-coordinate or the y-coordinate. For instance, the controller 70 may estimate the x-coordinate on an assumption that an average pupil distance of a human is 64 mm. The controller 70 specifically assumes that the examinee's pupil distance on the face image is 64 mm, and then calculates the y-coordinate and the z-coordinate.

In the present example, the alignment target is detected on the anterior segment image photographed by the anterior segment photographing optical system 60 to perform the final alignment, but the way of the alignment is not limited to this. Alternatively, the controller 70 may perform the final alignment from a pupil position on the anterior segment image, the contrast, the edge, and others.

<Audio Announcement>

The ophthalmic apparatus of the present example is configured to give an audio announcement to guide the examinee or the examiner. Specifically, the ophthalmic apparatus includes the speaker 79 as shown in FIG. 1. As shown in FIG. 2, the controller 70 is connected to the speaker 79. The controller 70 takes control of audio output of the speaker 79 and gives the audio announcement. To be specific, when the examinee is required to leave his/her face once from the jaw rest 11 in the step S150, or when the examinee is asked to blink an eye before measurement, the controller 70 gives the announcement. To give the audio announcement, the controller 70 may utilize the detected result from the sensor 113 (see FIGS. 1 and 2). The following explanation is given with the example of giving the announcement based on the output from the sensor 113.

(Step S151: Human Detection (1))

The apparatus of the present example determines the presence or the absence of the examinee and then performs the audio announcement. Specifically, the controller 70 determines the presence or the absence of a human by the output from the sensor 113. The controller 70 determines that the examinee is present when the controller 70 receives the output from the sensor 113. On the contrary, the controller 70 determines that the examinee is absent when there is no output from the sensor 113. In the case that the examinee is determined to be present, the controller 70 performs the similar processing with the steps S110 to S130 in FIG. 5, and then proceeds to a step S153. In the case that the examinee is determined to be absent, the controller 70 waits.

(Step S153: Determination of Jaw Rest Adjustment)

In a step S153, the controller 70 determines whether or not adjustment of the jaw rest is necessary. Specifically, the controller 70 estimates the position of the examinee's eye, and then determines whether or not there needs to adjust the jaw rest 11 as mentioned above. When the jaw rest 11 does not need to be moved, the controller 70 proceeds to a step S162. When the jaw rest 11 needs to be adjusted, the controller 70 proceeds to a step S154.

(Step S154: Determination of Jaw Rest Driving Amount)

In the step S154, the controller 70 determines a driving amount to move the jaw rest 11. Specifically, when the driving amount of the jaw rest 11 is smaller than the predetermined value, the controller 70 proceeds to a step S160. When the driving amount of the jaw rest 11 is larger than the predetermined value, the controller 70 proceeds to a step S155. In the controller 70, the predetermined value of the driving amount is stored in the memory part 74 or the like and may be arbitrarily set.

(Step S155: Audio Announcement (1))

In the step S155, the controller 70 gives an audio announcement of asking the examinee to leave the jaw from the jaw rest 11 before driving the jaw rest. For example, the controller 70 outputs the audio announcement such as "the jaw rest will be moved, please leave your jaw from the jaw rest" from the speaker 79.

(Step S156: Human Detection (2))

In a step S156, the controller 70 determines the presence or the absence of the examinee as similar to the step S151. It is thus confirmed that the examinee's jaw has left the jaw rest 11. Specifically, the controller 70 determines that the examinee's jaw has left the jaw rest when the output from the sensor 113 has ceased for several seconds. When it is determined that there is no examinee present, the controller 70 proceeds to the following step S157.

(Step S157: Jaw Rest Driving (1))

In the step S157, the controller 70 moves the jaw rest 11 by the driving amount of the jaw rest that is calculated based on the estimated position of the examinee's eye. The controller 70 may give an audio announcement before moving the jaw rest 11 that the jaw rest 11 will be moved again.

(Step S158: Audio Announcement (2))

When movement of the jaw rest 11 is completed, the controller 70 gives another announcement of asking the examinee to place the jaw on the jaw rest 11. Specifically, the controller 70 outputs an audio announcement such as "please place your jaw on the jaw rest."

(Step S159: Human Detection (3))

In a step S159, the controller 70 detects that the examinee has returned the jaw on the jaw rest 11. The controller 70 detects the output from the sensor 113, and subsequently, returns to the step S110.

(Step S160: Audio Announcement (3))

When the driving amount of the jaw rest 11 is determined to be small in the step S154, the controller 70 drives the jaw rest 11 while the jaw is being placed on the jaw rest 11. The controller 70 gives an audio announcement of notifying driving of the jaw rest 11 before driving the jaw rest 11. For example, the controller 70 outputs the announcement such as "the jaw rest will be moved."

(Step S161: Jaw Rest Driving (2))

In a step S161, the controller 70 drives the jaw rest 11. The controller 70 drives the jaw rest 11 to an appropriate position, and subsequently, returns to the step S110.

(Step S162: Audio Announcement (4))

In a step S162, the controller 70 gives an audio announcement from the speaker 79 notifying that the measurement is about to start. For example, the controller 70 outputs the announcement such as "measurement will be started" and "full-automatic alignment will be started."

(Step S163: Full-Automatic Alignment)

The controller 70 carries out the full-automatic alignment of the optometric part 2 with respect to the examinee's eye.

(Step S164: Audio Announcement (5))

The controller 70 gives an audio announcement of urging the examinee to be prepared for the measurement. Specifically, the controller 70 outputs the announcement such as "please blink an eye" and "please open your eye widely."

(Step S165: Measurement)

In a step S165, the controller 70 measures the examinee's eye. Specifically, the controller 70 irradiates the measurement light on the examinee's eye and receives the reflection light to examine the examinee's eye.

(Step S166: Audio Announcement (6))

The controller 70 subsequently gives an audio announcement of notifying termination of the measurement. For example, the audio announcement such as "the measurement has completed" is output. The controller 70 then gives an audio announcement of asking the examinee to leave the jaw rest 11. For example, the audio announcement such as "please leave the jaw rest" is output. The controller 70 further gives an announcement of initializing the position of the optometric part 2, the position of the jaw rest 11, and others. For example, the announcement such as "initialization will be performed" is given to perform the initialization.

(Step S167: Human Detection (4))

In a step S167, the controller 70 determines the presence or the absence of the examinee as similar to the step S151. Thus, it is confirmed that the examinee's jaw has left the jaw rest 11. When the examinee is determined to be absent, the controller 70 proceeds to a next step S168.

(Step S168: Initialization)

In the step S168, the controller 70 performs initialization of the apparatus. Specifically, the controller 70 returns the position of the optometric part 2 and the height of the jaw rest 11 to each of their initial positions. The initial position of the optometric part 2 is, for example, set in a position where the examinee's eye can be measured by slightly moving the eye therefrom. The initial position of the jaw rest 11 is, for example, set in a position of an average eye level.

As mentioned above, the ophthalmic apparatus of the present example is configured to notify the movement of the optometric part 2 or the jaw rest 11 to the examinee in advance, and thus it is prevented that the examiner or the examinee gets surprised at any unexpected operation of the apparatus. Further, the ophthalmic apparatus 1 is configured to perform the audio announcement to ask the examinee to leave the face so that the examinee's face would not be caught by the jaw rest 11 and the forehead support 10 when the jaw rest 11 is about to be largely moved. The ophthalmic apparatus of the present example performing the full-automatic alignment is configured to automatically perform the measurement, initialization, jaw rest driving, but the measurement can be performed safely by notifying the examinee of a timing of starting each operation. Further, the audio announcements by the speaker can omit the examiner's labor of oral instructions.

Some ophthalmic apparatuses are better to make the examinee blink an eye before testing. Such apparatuses are, for example, a perimeter requiring long time for testing, a non-contact tonometer configured to blow air or the like, and a fundus camera irradiating a strong light. In this case, the ophthalmic apparatus 1 gives the announcement of urging the examinee to be prepared before measurement as indicated in the step S166, and thus the measurement can be performed stably. For example, the examinee's blinking of the eye can expect reduction in blinks during the measurement, prevention of dryness of the eye, removal of excessive tears, and others. The controller 70 may further give an announcement of asking the examinee to blink when it is detected from the anterior segment image that the eye has got dry and a brightness spot becomes blurred.

Further, some ophthalmic apparatuses need the examinee to open the eye widely before testing. For example, apparatuses such as an eye refractive power measuring apparatus, a non-contact tonometer, and a fundus camera are better to be measured stably with a wide-opened eye of the examinee. When the test is to be performed by this type of apparatus, the audio announcement of asking the examinee to open the eye widely before the measurement may be given as indicated in the step S166. At this time, an opening degree of the examinee's eye may be detected from the anterior segment image photographed by the anterior segment photographing optical system 60, and when the eye is determined not to be opening enough, the audio announcement of asking the examinee to open the eye wider may be given. As above, by obtaining feedback from the anterior segment image, the audio announcement may be given only when it is necessary according to an opening state of the eye.

In a case that one eye is kept closing during the measurement, there is a possibility that fixation of the eye becomes unstable or the eye cannot be opened wide enough. To address those problems, another announcement of asking the examinee to open both eyes during the measurement may be given. For example, the controller 70 may output the announcement such as "please open both eyes."

An ophthalmic apparatus such as the fundus camera, a corneal shape measuring apparatus, and a tonometer may require operations of making a nozzle approach toward the eye, blowing air, making a sound, and others. In these types of the apparatuses, an announcement of notifying the following operation in advance may be given so that the examinee would not get surprised. The announcement includes "a strong light will be irradiated," "a nozzle will approach," "air will be blown," and "sound will be given,"

for example. These announcements can prevent the examinee from getting surprised to release his/her face from the face support part 9.

The controller 70 may further give an announcement of explaining a testing procedure to the examinee. For example, there may be output an announcement of "please look into the apparatus. When you see flashing green lights, please open your both eyes widely and look into the flashing green lights without blinking as much as possible." Accordingly, even if the examinee is unsure about the testing procedure, a test can be appropriately performed.

The controller 70 may further give an announcement of calling attentions during the test. For example, the controller 70 may give an audio announcement of instructing the examinee not to blink eyes during the measurement. To be specific, there may be an announcement of "please refrain from blinking as much as possible during the measurement."

An apparatus such as a visual field measurement apparatus requiring long time for measurement may give an audio announcement for maintaining the examinee's concentration. For example, the controller 70 may give announcements such as "a fixation light is displaced," and "20% of the entire measurement has finished." Thus, the examinee can understand the testing situation and concentrate on the testing.

Furthermore, the controller 70 may give an announcement for relaxing the examinee during the measurement. For example, there may be an announcement such as "please look into a target and be relaxed." Thus, it is possible to lessen the examinee's burden due to a continuing tensed state.

The controller 70 may further give an audio announcement of switching the left and right eyes. Specifically, in the above step S400, there may be an announcement such as "next, a left eye will be examined." The examinee can thus understand that the other eye will be measured after the one eye is finished with the measurement, thereby preventing unexpected movement of the examinee. Accordingly, the measurement can be performed smoothly.

The controller 70 may further give an announcement of notifying which test will be subsequently performed at the time of switching a measurement mode. The examinee can thus understand which test is about to be performed, thus removing the examinee's anxiety. The controller 70 may further output a sound of shutter by a photographing apparatus such as the fundus camera. Thereby, the examinee can understand that he/she is being photographed, and thus the examinee can pay attention not to move the face or the eyes.

When the examinee's eye cannot be detected or measured, the controller 70 may give an audio announcement that the measurement cannot be performed. Furthermore, the controller 70 may give an audio announcement of instructing the examinee to call the examiner. Accordingly, even when the examiner stays in a far position at the time of measurement, the examinee does not have to wait wastefully at the site of testing, so that it is expected that the time for testing can be shortened.

The controller 70 may further give an announcement of asking the examinee to take off glasses or contact lenses in advance of the measurement. For example, the controller 70 may output an announcement such as "please take off your glasses or contact lenses." Accordingly, it is possible to prevent a mistake of conducting a test while the glasses or the contact lenses are put on. Furthermore, when a patient's visibility is out of a focus adjustment range of the apparatus, for example, the controller 70 may give an audio announcement of asking the patient to put on the glasses. Specifically, the controller 70 may output an announcement such as "please put on your glasses or contact lenses."

The controller 70 may further give an audio announcement of indicating a correct way of placing the face on the face support part 9. Specifically, the controller 70 may give an audio announcement such as "please place your jaw deeply on the jaw rest and make your forehead slightly contact with the forehead support." The controller 70 may further give an announcement such as "please lightly hold grips on both left and right sides of the jaw rest with your both hands." Thus, the examinee can take the measurement in the right posture.

After termination of the measurement, the controller 70 may give an announcement of asking the examinee to slowly leave the head from the jaw rest. Further, the controller 70 may give an announcement of asking the examinee not to hold the jaw rest 11 and the forehead support 10 when the examinee is about to stand up. Thus, it is possible to prevent breakage on the apparatus or prevent the examinee from getting hurt after the measurement.

The controller 70 may further give an audio announcement of asking the examinee to blink the eyes and wait for a while to rest the eyes after the measurement.

<From Measurement Preparation to Measurement>

Figure 11:
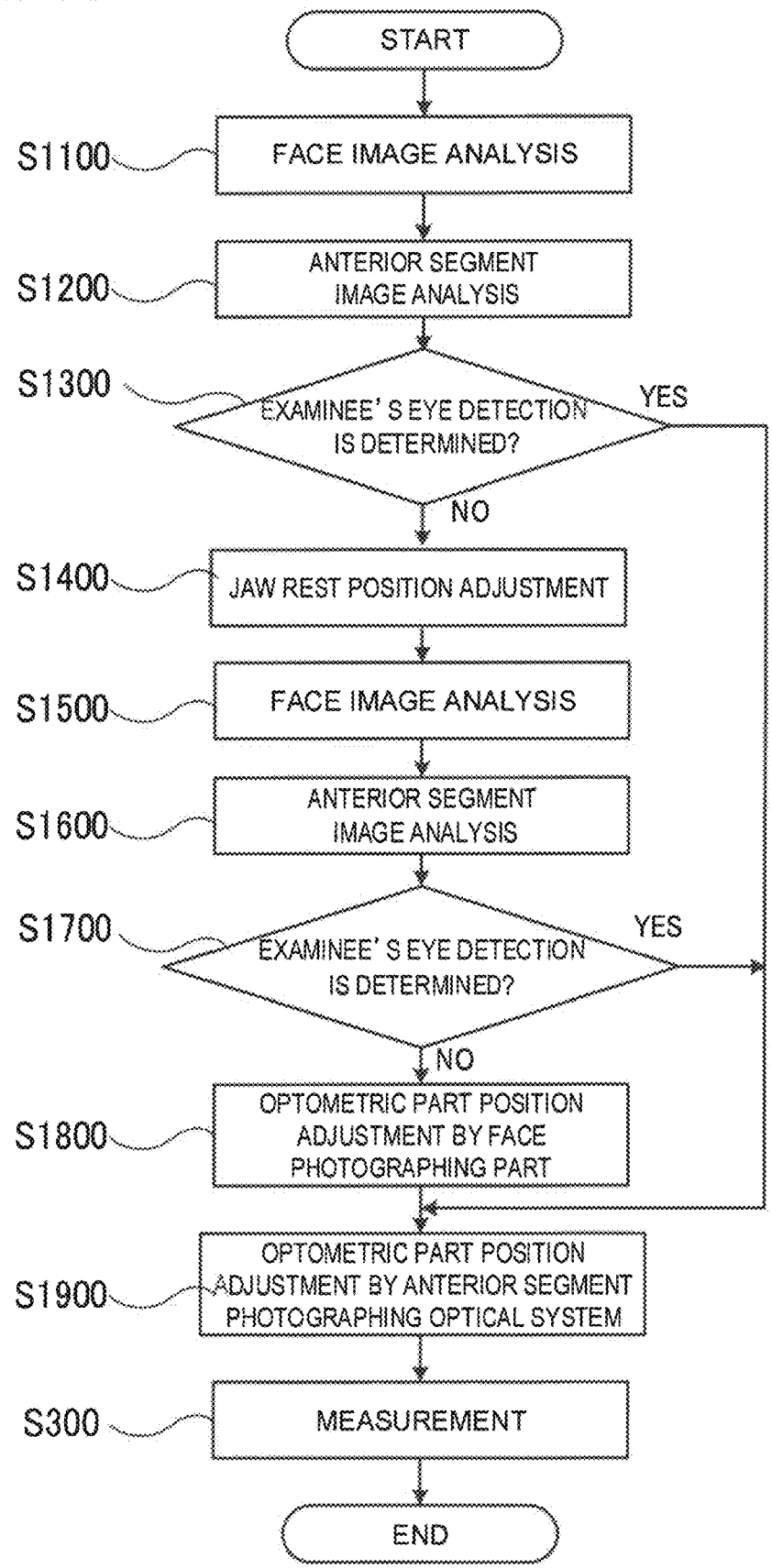
FIG. 11 is a flow chart showing an operation control of full-automatic alignment of the present example.

A control process from a preparation of measurement in the step S100 to the measurement in the step S300 is now explained in detail with reference to FIG. 11. Specifically, the controller 70 detects both eyes of the examinee from a face image photographed by the face photographing part 90.

(Step S1100: Face Image Analysis)

In a step S1100, the controller 70 places the optometric part 2 in a predetermined initial position. At this time, the controller 70 may place the optometric part 2 in an initial position which has been stored in the memory part 74. The controller 70 may control a position detection sensor 75 to detect arrival of the optometric part 2 at the initial position for placing the optometric part 2 in the initial position. The controller 70 illuminates the face by a face illumination optical system 80 and further detects a position of at least one of the examinee's left and right eyes based on a photographed signal from the face photographing part 90.

(Step S1200: Anterior Segment Image Analysis)

In a step S1200, the controller 70 analyzes an anterior segment image based on the photographed signal from the anterior segment photographing optical system 60 to perform detection and processing of the examinee's eye. To be specific, the controller 70 analyzes the anterior segment image and then detects the target or the featured portion of the eye.

(Step S1300: Determination of Examinee's Eye Detection)

In a step S1300, the controller 70 determines whether or not the examinee's eye is detected based on the photographed signal from the anterior segment photographing optical system 60 in the detection processing in the step S1200. When the examinee's eye is detected, the controller 70 skips a jaw rest adjustment in a step S1400 and proceeds to a positional adjustment of the optometric part 2 by the anterior segment photographing optical system 60. When the examinee's eye is not detected, the controller 70 proceeds to the step S1400.

(Step S1400: Jaw Rest Adjustment)

In the step S1400, the controller 70 specifically controls the jaw rest driving part 12 to adjust the height of the jaw rest. The controller 70 controls the jaw rest driving part 12 based on the analysis result in the step S1100 to adjust the height of the jaw rest. In this case, the controller may control the jaw rest driving part 12 such that the examinee's eye is placed within a movable range of the optometric part 2 and adjust the height of the jaw rest. When the jaw rest adjustment is not necessary, the controller may proceed to a step S1800.

(Step S1500: Second Face Image Analysis)

After the adjustment of the height of the jaw rest has been completed, the controller 70 detects at least one of the left and right eyes based on the photographed signal from the face photographing part 90 in a step S1500.

(Step S1600: Second Anterior Segment Image Analysis)

In a step S1600, the controller 70 analyzes the anterior segment image based on the photographed signal from the anterior segment photographing optical system 60, and then detects the examinee's eye.

(Step S1700: Second Determination of Examinee's Eye Detection)

In a step S1700, the controller 70 determines whether or not the examinee's eye is detected in the detection processing in the step S1600. When the examinee's eye is determined to be detected, the controller 70 skips a positional adjustment of the optometric part 2 by the face photographing part 90 and proceeds to the positional adjustment of the optometric part 2 by the anterior segment photographing optical system 60. When the examinee's eye is not detected, the controller proceeds to the step S1800.

(Step S1800: Positional Adjustment by Face Photographing Part)

In the step S1800, the controller 70 controls the driving part 4 based on the photographed signal from the face photographing part 90 to adjust the position of the optometric part 2. The controller 70 then detects the position of the eye based on the photographed signal from the face photographing part 90. The controller 70 controls the driving part 4 based on the position detection result and adjust the three-dimensional position of the optometric part 2. In this case, the controller may control the driving part 4 such that the examinee's eye is placed within an allowable photographing range of the anterior segment photographing optical system 60 to adjust the position of the optometric part 2.

(Step S1900: Positional Adjustment by Anterior Segment Photographing Optical System 60)

In a step S1900, the controller 70 controls the driving part 4 based on the photographed signal from the anterior segment photographing optical system 60 to adjust the position of the optometric part 2. The controller 70 detects the position of the examinee's eye based on the photographed signal from the anterior segment photographing optical system 60. The controller 70 controls the driving part 4 based on the position detection result to adjust the position of the optometric part 2. In this case, the controller may control the driving part 4 such that the examine's eye is placed within an allowable range of alignment to adjust the three-dimensional position of the optometric part 2.

<Setting Region of Interest (ROI) in Automatic Gain Control>

Figure 12:
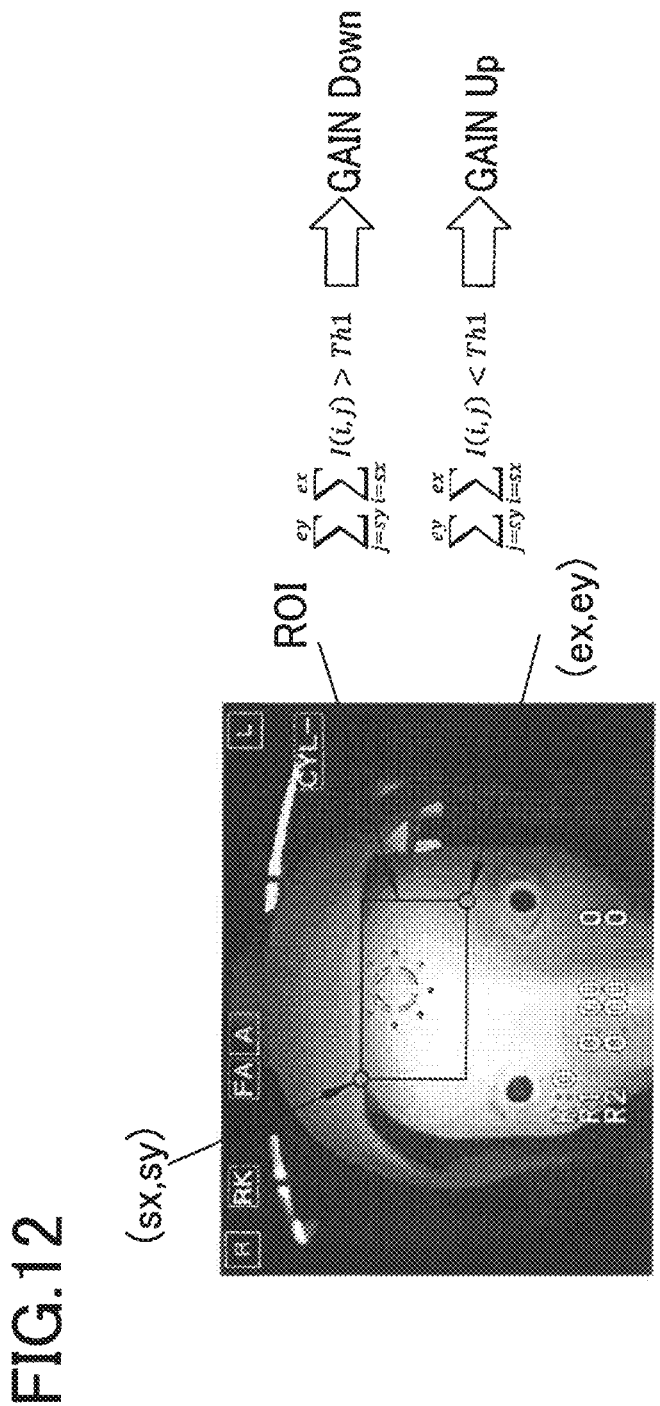
FIG. 12 is a view showing an example of an automatic gain control.

Now explained is one example of performing an automatic gain control of the face photographing part 90 in analyzing the face image in the step S1100. FIG. 12 is a view showing one example of the automatic gain control. The controller 70 sets a region of interest (ROI) based on the optometric part that has been placed in its initial position on the photographed image photographed by the face photographing part 90. In this case, the ROI represents a region of interest which is set for performing the automatic gain control.

Specifically, when the examinee supported by the jaw rest 11 is photographed in the initial position, an imaging region that is highly possibly set as a face region is set in advance as the ROI. Thus, the gain is automatically adjusted such that a luminance in the ROT is set as a target value.

Specifically, the controller carries out the automatic gain control such that the luminance in the ROI becomes a target value Thl. To be more specific, the controller may perform the automatic gain control such that a luminance accumulated value of each pixel in the ROT approaches the predetermined target value Thl. When the luminance accumulated value is less than the target value, the gain may be increased, and when the luminance accumulated value is more than the target value, the gain may be reduced.

Accordingly, in the photographed image photographed by the face photographing part 90, which tends to collect ambient light due to its wide angle, the contrast of the examinee's face and the eye can be appropriately adjusted, thus achieving smooth detection of the eye in the following steps.

Herein, another automatic gain control may be performed (for example, in steps S1500, S1800, and others) after the automatic gain control in the initial position or may not be carried out and just ended. Alternatively, the automatic gain control may be continuously performed.

Figure 13:
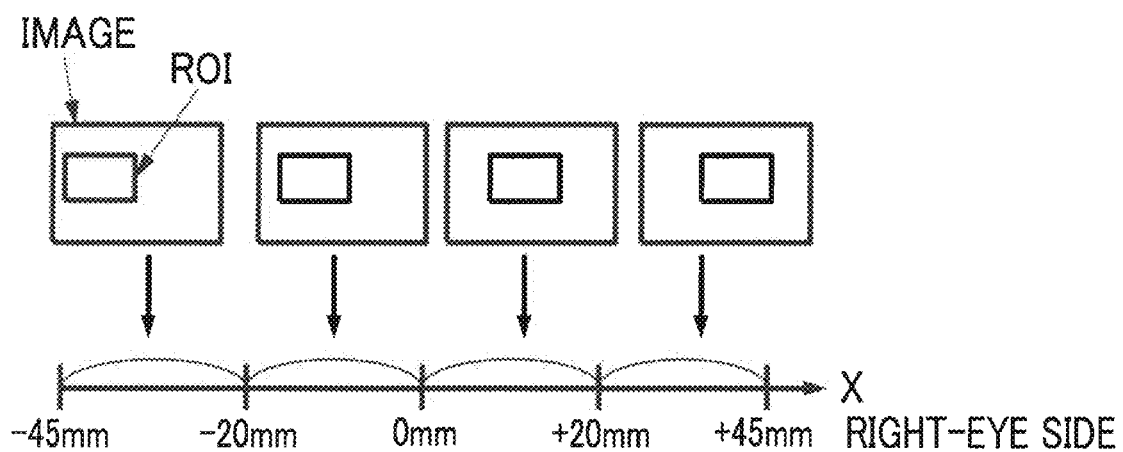
FIG. 13 is a schematic view showing an example of switching a position of a region of interest corresponding to a position of an optometric part.

After performing the automatic gain control in the initial position, the controller may move the ROI according to a position of the optometric part 2. FIG. 13 is a view showing an example of switching the position of the ROT according to the position of the optometric part 2. In the present example, a plurality of different ROIs are set according to a lateral (left and right) position of the optometric part 2. In this case, a transfer amount of the optometric part 2 in the left and right direction and a moving amount of the ROI in the photographed image may be correspondingly related.

A size of the ROI in the photographed image may be arbitrarily set according to a purpose of image processing. The present example is directed to appropriately perform favorable eye detection by properly adjusting the luminance of the face, and thus the ROI is set with a size large enough to form an image of at least a part of the examinee's skin (preferably in a position avoiding eyes). In this case, each boundary corresponding to the ROI for each of the up and down direction and the left and right direction may be set. As another example, the boundary corresponding to the ROI only for the left and right direction may be set.

The corresponding relation of the position of the optometric part 2 and the set position of the ROI may be stored in advance in the memory part 74, and the controller 70 may set the ROI according to the position of the optometric part 2 by use of the thus stored corresponding relation stored in the memory part 74. The corresponding relation of the position of the optometric part 2 and the set position of the ROI may be obtained by a simulation that considers each position of the optometric part 2 and the face photographing part 90 of the optometric part 2. Further, the corresponding relation of the position of the optometric part 2 and the set position of the ROI may be obtained by actually photographing the examinee's face by the face photographing part 90 while the face is being supported by the jaw rest 11.

In FIG. 13, four different types of ROI are set according to the left and right position, but the number of ROI is not limited to this. Two or three types of ROIs may be set, or five or more ROIs may be set. Further alternatively, the ROI may be linearly set according to the position of the optometric part 2.

The controller 70 may vary the set position of the ROI on the photographed image based on the positional information of the optometric part 2 from the position detection sensor 75 and perform the automatic gain control based on the image signal in the thus changed ROI. Accordingly, the ROI can be set in an appropriate position with no regard to the position of the optometric part 2, and thus the automatic gain control can be appropriately performed.

The controller 70 carries out the automatic gain control by setting the ROI according to the position of the optometric part 2, and thus gain adjustment can be performed corresponding to a position of forming the face image on the photographed image, which is more advantageous. In other words, there is a case that adjustment of the photographed image is required due to different illumination state of the face illumination depending on the position of the optometric part 2. To address this, the ROI set according to the position of the optometric part 2 as mentioned above is used for another automatic gain control, making it possible to respond to changes in the illumination state and preferably perform the alignment based on the eye detection by use of the face photographing part 90. Further, the position of the ROI is changed according to the position of the optometric part 2, and thus, irrespective of the position of the optometric part 2, the brightness of the face is adjusted to a certain target level irrespective of the brightness of an exterior lighting or the like, thereby surely achieving the eye detection and others.

In the above explanation, the position of the ROT is changed according to the position of the optometric part 2 to carry out the automatic gain control, but the control method is not limited to this. The illumination state of the face illumination may be changed according to the position of the optometric part 2.

Figure 14:
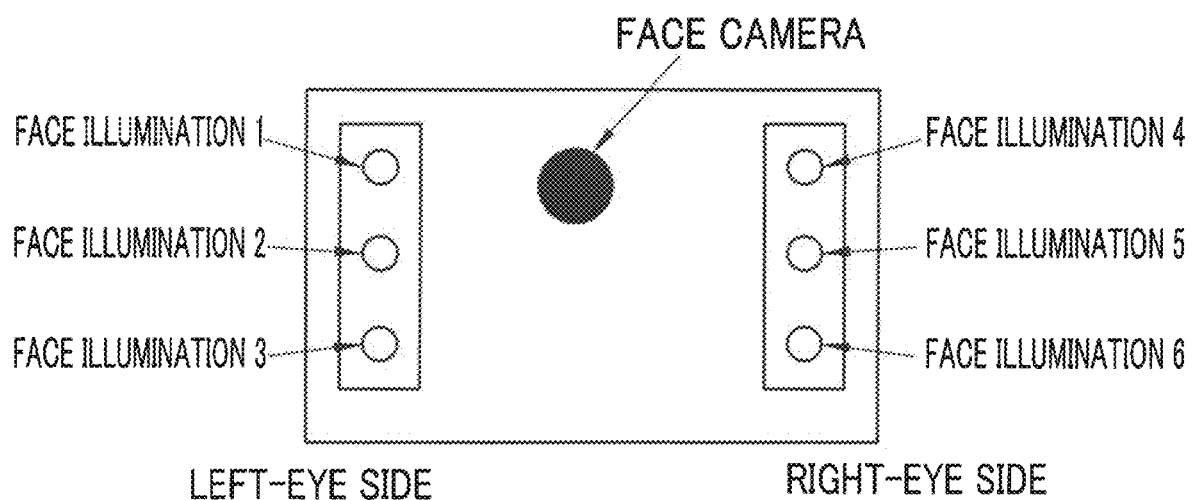
FIG. 14 is a schematic view showing an example of changing a face illumination corresponding to the position of the optometric part.

FIG. 14 shows one example of changing the face illumination according to the position of the optometric part 2. For example, when the optometric part 2 is moved toward the left eye, face illuminations 1 to 3 are turned on and the face illuminations 4 to 6 are turned off. When the optometric part 2 is moved toward the right eye, the face illuminations 4 to 6 are turned on and the face illuminations 1 to 3 are turned off. When the optometric part 2 is placed in a center position, the face illuminations 1 to 6 may be turned on. As an alternative for limiting to light on or off of the plurality of illumination light sources, each illumination light amount of the light sources may be adjusted. A positional configuration of the face illumination is not limited to the above, and may be varied in various ways. Further, each of the face illuminations 1 to 6 may be individually controlled its light amount according to the position of the optometric part 2.

<Setting Region of Interest for Eye Detection>

One example of performing the eye detection in the face image analysis in the steps S1100, S1500, S1800, and others is now explained.

The controller 70 sets the ROI based on the position of the optometric part on the photographed image photographed by the face photographing part 90. In this example, the ROI is the region of interest that is set for performing the eye detection and further set as an image search range for the eye detection.

In the present example, the eye is detected by the face photographing part 90. For detecting the eye, limitation of the search range on the photographed image can achieve acceleration of the detection processing and reduction in erroneous detection (detecting something different as an eye), for example. In this example, the position of the eye is changed according to the position of the optometric part 2, and thus the ROI (image search range) is set based on the three-dimensional position of the optometric part 2 to search the eye in the ROI.

In photographing the face while the face is placed on the jaw rest 11, a possible area of the eye to be existed on the three-dimensional actual space is limited to a certain degree. This is because a pupil distance and a size of the face are different in each individual, but they exist within a certain range. Accordingly, it is obtained that which region on the photographed image photographed by the face photographing part 90 becomes an actual space region where the eye exists, and the thus obtained region is set as a region to be searched.

The following explanation includes a method of setting a region of interest (a region where an eye is considered to exist) in a three-dimensional actual space, a method of transforming the ROI on the actual space into a coordinate on the photographed image, a method of calibrating a result of coordinate transformation in consideration of lens distortion of the face photographing part 90, and a method of obtaining the region of interest (the region where the eye is considered to exist) on the image from the calibrated result of the coordinate transformation.

Figure 15:
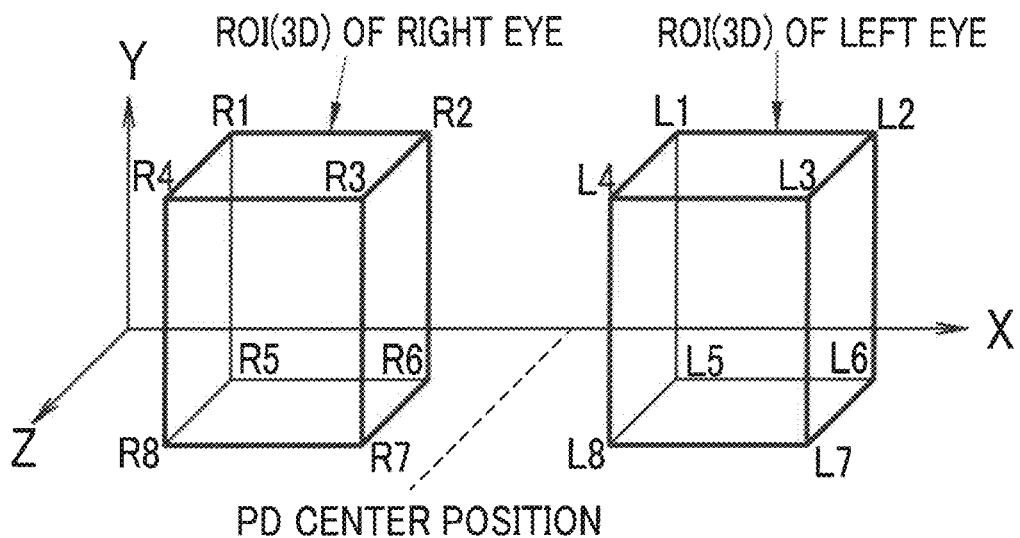
FIG. 15 is a schematic view showing an example of a solid region where left and right eyes are considered to exist in a three-dimensional actual space.

On the three-dimensional actual space, there is set a solid region where a right eye is considered to exist when the examinee places his/her face on the jaw rest 11 (see FIG. 15). This solid space is constituted of apexes R1 to R8, and each of the apexes are represented as R1=(XR1, YR1, ZR1), . . . , R8=(XR8, YR8, ZR8). Similarly, there is set a rectangular parallelpiped constituted of apexes L1 to L8 in which a left eye is considered to exist.

For example, in the left and right direction, any one point on a plane formed by linking the apexes R1-R5-R8-R4 represents a position of the right eye assuming the examinee's eye having the largest pupil distance (specifically, PD=90 mm). This position is specifically set in a position apart from a center position of the apparatus by 45 mm. Further, any one point on a plane formed by linking the apexes R2-R6-R7-R3 represents a position of the right eye assuming the examinee's eye having the smallest pupil distance (specifically, PD=30 mm). This position is specifically set in a position apart from the center position of the apparatus by 15 mm. The center position may be a center of a movable range of the driving part in the left and right direction or may be a bilateral symmetrical axis of the apparatus body (such as the base and the face support part).

With respect to the up and down direction, any one point on a plane formed by apexes R1-R2-R3-R4 is an upper limit of the movable range of the optometric part 2. To be more specific, the position is set upward away from a position of an eye level marker by 32 mm. Any one point on a plane formed by apexes R5-R6-R7-R8 is a lower limit of the movable range of the optometric part 2. To be more specific, the position is set downward away from the position of the eye level marker by 32 mm.

With respect to a Z-direction, any one point on a plane formed by the apexes R3-R7-R8-R4 is set in a position shifted toward the apparatus by a predetermined amount (for example, by 20 mm) away from an average eye position when the examinee is supported by the face support part 9. Further, any one point on a plane formed by the apexes R2-R6-R5-R1 is set in a position shifted toward the examinee by a predetermined amount (for example, by 20 mm) away from the average eye position when the examinee is supported by the face support part 9. The similar method is applied for the left eye, and thus the explanation thereof is omitted.

Figure 16:
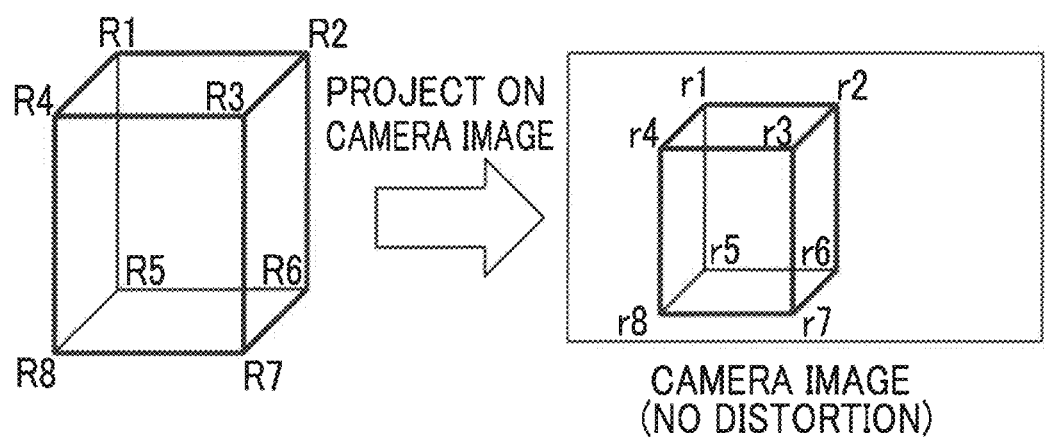
FIG. 16 is an explanatory view for explaining the way of obtaining where on a photographed image apexes of a solid in the region of interest in the actual space are projected.

It is obtained where on the photographed image the above-determined apexes of the solid in the ROI in the actual space are projected (see FIG. 16). An explanation is given by presenting a method of obtaining the ROI of the right eye on the photographed image. Firstly, R1 to R8 are assumed to be projected as r1 to r8 on the camera, respectively. Each point is indicated as r1=(xr1, yr1), ..., r8=(xr8, yr8). These r1 to r8 are obtained.

When a pinhole camera model is adapted, from a relation of projecting the three-dimensional coordinate on the two-dimensional coordinate on the photographed image, the following formula (12) is satisfied between R1=(XR1, YR1, ZR1) and r1=(xr1, yr1):

$$h \begin{pmatrix} x_{r1} \\ y_{r1} \\ 1 \end{pmatrix} = \begin{pmatrix} c_{11} & c_{12} & c_{13} & c_{14} \\ c_{21} & c_{22} & c_{23} & c_{24} \\ c_{31} & c_{32} & c_{33} & c_{34} \end{pmatrix} \begin{pmatrix} X_{R1} \\ Y_{R1} \\ Z_{R1} \\ 1 \end{pmatrix} \quad (12)$$

The following formula $$\begin{pmatrix} c_{11} & c_{12} & c_{13} & c_{14} \\ c_{21} & c_{22} & c_{23} & c_{24} \\ c_{31} & c_{32} & c_{33} & c_{34} \end{pmatrix} \quad (13)$$

is a camera parameter matrix of the face photographing part 90. The camera parameter includes an internal parameter representing a focal position and an optical center of the face photographing part 90 and an external parameter representing an orientation and a position of the face photographing part 90. Values c11 to c34 are obtained by values measured by prior calibration and three-dimensional positional information of the optometric part 2 which is detected by the position detection sensor 75. The formula (1) is developed to obtain the following formula (14):

$$\begin{cases} x_{r1} = \dfrac{c_{11}X_{R1} + c_{12}Y_{R1} + c_{13}Z_{R1} + c_{14}}{c_{31}X_{R1} + c_{32}Y_{R1} + c_{33}Z_{R1} + c_{34}} \\ y_{r1} = \dfrac{c_{21}X_{R1} + c_{22}Y_{R1} + c_{23}Z_{R1} + c_{24}}{c_{31}X_{R1} + c_{32}Y_{R1} + c_{33}Z_{R1} + c_{34}} \end{cases} \quad (14)$$

Coordinates l1 to l8 projecting the apexes L1 to L8 on the camera can be obtained as similar to the above.

Figure 17:
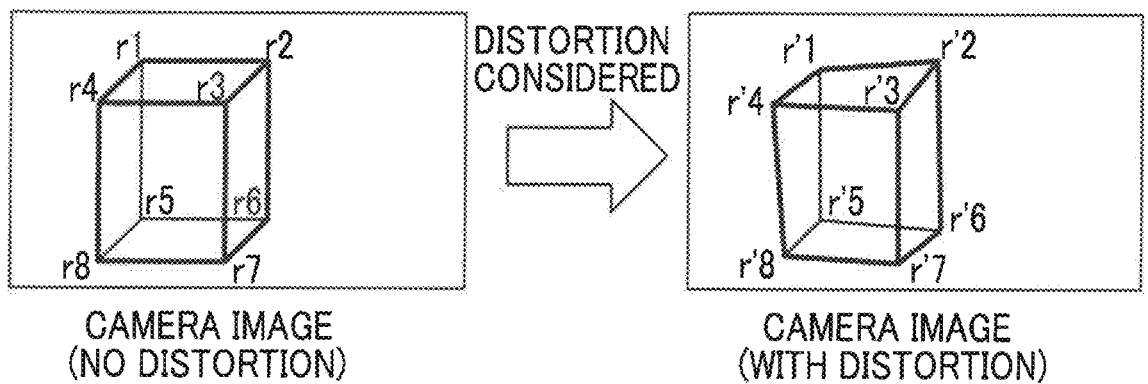
FIG. 17 is an explanatory view for explaining distortion of a camera image.

In the present example, there occurs distortion on the photographed image photographed by the face photographing part 90 (see FIG. 17). In the present example, detection of the eye is performed with the original image (distortion correction is not performed). The distortion correction may be performed even though the distortion correction in image processing does not have to be performed when there is less influence of distortion.

The above obtained coordinates r1 to r8 are not considered with distortion. These coordinates r1 to r8 with no distortion are converted into coordinates r'1 to r'8 which are considered with distortion. An explanation is made with an example of converting r1 (xr1, yr1) to r'1 (x'r1, y'r1). The relation of r1 and r'1 is represented by the following formula (15):

$$\begin{cases} x'_{r1} - x_c = (x_{r1} - x_c)(1 + k_1 m^2 + k_2 m^4 + k_3 m^6) \\ y'_{r1} - y_c = (y_{r1} - y_c)(1 + k_1 m^2 + k_2 m^4 + k_3 m^6) \end{cases} \quad (15)$$

A coordinate (xc, yc) in the formula (15) represents an optical center coordinate on the image, k1 to k3 represent distortion coefficients, and m indicates a radius from the optical center on the image. The relation is further represented by the following formula (16):

$$m = \sqrt{(x_{r1} - x_c)^2 + (y_{r1} - y_c)^2} \quad (16).$$

The coordinate r'1 is obtained by the formula (3). Similarly, the coordinates r'2 to r'8 are obtained. Further similarly, the coordinates l1 to l8 with no distortion are converted into coordinates l'1 to l'8 which are considered with distortion.

Figure 18:
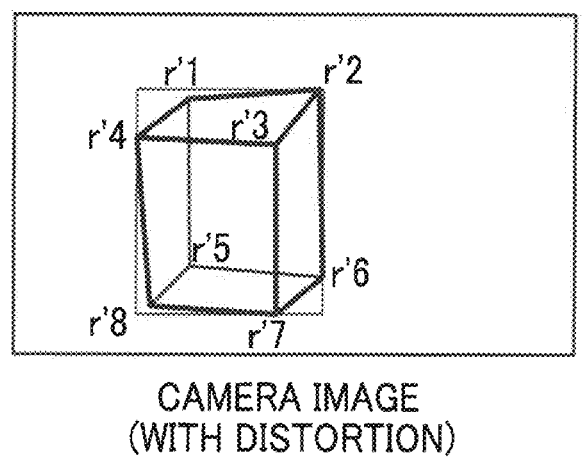
FIG. 18 is a schematic view showing an example of setting the region of interest based on a three-dimensional position of the optometric part on the photographed image photographed by a face photographing part.

The ROI of the right eye on the photographed image is determined to be within the minimum rectangular region including all the coordinates r'1 to r'8 (see the rectangular ROI in FIG. 18). Similarly, the ROI of the left eye is determined to be within the minimum rectangular region including all the coordinates l'1 to l'8.

By use of the above method, the controller 70 sets the ROI based on the position of the optometric part 2. The controller 70 performs processing of the image signal in the set ROI and searches the eye existing in the ROI to perform the eye detection.

Modified Examples

<Parallel Performance of Face Photographing and Anterior Segment Photographing>

The controller 70 may perform the eye detection by the face photographing part 90 even after performing the eye detection by the anterior segment photographing optical system 60. For example, if the examinee's face is moved after detecting the eye by the optical system 60, there is a possibility that the eye could not be detected from the photographed image photographed by the optical system 60, and the position of the eye could not be detected.

The controller 70 may perform the eye detection by the face photographing part 90 in parallel even after detecting the eye by the anterior segment photographing optical system 60. The eye detection by the face photographing part 90 may be continuously performed in parallel or alternately with the eye detection by the image taken by the optical system 60.

Accordingly, even after the eye detection by the anterior segment photographing optical system 60, the position of the eye can be detected in a wide range by the face photographing part 90, achieving smooth alignment with no need to return the apparatus to the initial position again. In this case, the controller 70 may restore the eye detection by the face photographing part 90 only when the eye could not be detected by the anterior segment photographing optical system 60.

REFERENCE SIGNS LIST

1 Ophthalmic apparatus
2 Optometric part
4 Driving part
5 Base
6 Housing
9 Face support part
11 Jaw rest 70 Controller
71 CPU
72 ROM
73 RAM
90 Face photographing part

What is claimed is:

1. An ophthalmic apparatus for examining an examinee's eye, the apparatus comprising:
a face support part configured to support an examinee's face and including (i) a jaw rest configured to support the examinee's jaw and (ii) a jaw rest driving part configured to drive the jaw rest;
a human detection part configured to detect whether the face is supported by the face support part;
a notification part configured to give an audio announcement to the examinee; and
a controller (i) configured to control the notification part based on a detection result of the human detection part to give an audio announcement of moving the jaw rest and (ii) configured to move the jaw rest by controlling the jaw rest driving part, wherein
when the examinee's face is determined from the detection result to be supported by the face support part, the controller is configured to control the notification part to give an announcement of asking the examinee to remove the jaw from the jaw rest in advance of driving the jaw rest by the jaw rest driving part, and
the controller is configured to move the jaw rest by controlling the jaw rest driving part after controlling the notification part to give the audio announcement asking the examinee to remove the jaw.

2. The ophthalmic apparatus according to claim 1, wherein the controller is configured to control the jaw rest driving part to drive the jaw rest when the examinee's face is determined from the detection result not to be supported by the face support part.

3. The ophthalmic apparatus according to claim 1, wherein the controller is configured to change a content of the announcement according to a driving amount to move the jaw rest to an appropriate position.

4. The ophthalmic apparatus according to claim 3, wherein the controller is configured to control the notification part to give the announcement of asking the examinee to remove the jaw from the jaw rest when the driving amount is large and give the announcement of moving the jaw rest when the driving amount is small.

5. The ophthalmic apparatus according to claim 1, further comprising:
a driving part configured to drive an optometric part for examining the examinee's eye, wherein
the controller is configured to control the notification part to give an announcement of calling an attention when at least one of the optometric part and the jaw rest is returned to an initial position by the driving part or the jaw rest driving part.

6. The ophthalmic apparatus according to claim 1, wherein the controller is configured to control the notification part to give an announcement of urging the examinee to make a blink.

7. The ophthalmic apparatus according to claim 6, further comprising a blink detection part, wherein
the controller is configured to control the notification part to give the announcement of urging the examinee to make a blink and start a test of the examinee's eye after the blink detection part detects the examinee's blink.

8. The ophthalmic apparatus according to claim 1, wherein the controller is configured to control the notification part to give an announcement of changing an object to be examined when the object to be examined is changed from any one of right and left eyes to the other eye.

9. The ophthalmic apparatus according to claim 1, wherein the controller is configured to move the jaw rest by controlling the jaw rest driving part after controlling the notification part to give the audio announcement of moving the jaw rest.

10. The ophthalmic apparatus according to claim 1, wherein the controller is configured to control the notification part to give an audio announcement of asking the examinee to open the eye widely before measurement.

11. The ophthalmic apparatus according to claim 1, wherein the controller is configured to control the notification part to give the announcement of asking the examinee to remove the jaw from the jaw rest while the examinee's face is supported by the face support part.

12. The ophthalmic apparatus according to claim 1, further comprising a face photographing part configured to obtain a face image including at least one of the examinee's eyes, wherein
the controller is configured to determine a necessity of moving the jaw rest based on the obtained face image, and
the controller is configured to control the notification part to give the announcement of asking the examinee to remove the jaw from the jaw rest when (i) moving the jaw rest is determined to be necessary based on the obtained face image and (ii) the examinee's face is determined from the detection result of the human detection part to be supported by the face support part.

* * * * *